United States Patent
Ellmark et al.

(10) Patent No.: US 9,834,589 B2
(45) Date of Patent: *Dec. 5, 2017

(54) CD86 VARIANTS WITH IMPROVED AFFINITY FOR CTLA-4

(71) Applicant: ALLIGATOR BIOSCIENCE AB, Lund (SE)

(72) Inventors: Peter Ellmark, Lund (SE); Christina Furebring, Lund (SE); Eva Dahlen, Lund (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/901,202

(22) PCT Filed: Jun. 25, 2014

(86) PCT No.: PCT/EP2014/063442
§ 371 (c)(1),
(2) Date: Dec. 28, 2015

(87) PCT Pub. No.: WO2014/207063
PCT Pub. Date: Dec. 31, 2014

(65) Prior Publication Data
US 2016/0304580 A1    Oct. 20, 2016

(30) Foreign Application Priority Data

Jun. 27, 2013 (GB) .................................. 1311475.6

(51) Int. Cl.
| C07K 14/705 | (2006.01) |
| A61K 38/16  | (2006.01) |
| G01N 33/566 | (2006.01) |
| A61K 38/00  | (2006.01) |

(52) U.S. Cl.
CPC ..... *C07K 14/70532* (2013.01); *G01N 33/566* (2013.01); *A61K 38/00* (2013.01); *G01N 2333/70532* (2013.01); *G01N 2500/04* (2013.01)

(58) Field of Classification Search
CPC .............. C07K 14/70532; A61K 38/00; G01N 33/566; G01N 2333/70532; G01N 2500/04
See application file for complete search history.

(56) References Cited

U.S. PATENT DOCUMENTS

| 5,637,481 A | 6/1997 | Ledbetter et al. |
| 6,130,316 A | 10/2000 | Freeman et al. |
| 2003/0138881 A1 | 7/2003 | Punnonen et al. |
| 2008/0233122 A1 | 9/2008 | Hanson et al. |

FOREIGN PATENT DOCUMENTS

| EP | 1186300 | 3/2002 |
| WO | WO 02/48351 | 6/2002 |
| WO | WO 03/097834 | 11/2003 |
| WO | WO 2006/056464 | 6/2006 |
| WO | WO 2007/057682 | 5/2007 |

OTHER PUBLICATIONS

Water, from http://www.biology-online.org/dictionary/Water, pp. 1-3, accessed Apr. 24, 2014.*
"SubName: Full=T-lymphocyte activation antigen CD86," EBI assession No. UNIPROT: L8YBM3, Apr. 2013, 1 page.
"RecName: Full=T-lymphocyte activation antigen CD86," EBI assession No. UNIPROT: P42071, Nov. 1995, 2 pages.
Subname: Full=CD86 variant, EBI accession No. UNIPROT: Q5MD24, Feb. 2005, 1 page.
Biburger et al. "A Novel Bispecific Tetravalent Antibody Fusion Protein to Target Costimulatory Activity for T-cell Activation to Tumor Cells Overexpressing ErbB2/HER2," Journal of Molecular Biology, Mar. 2005, vol. 346, No. 5, pp. 1299-1311.
Broeren et al. "Costimulation Light: Activation of CD4+ T Cells with CD80 or CD86 Rather Than Anti-CD28 Leads to a Th2 Cytokine Profile," The Journal of Immunology, Dec. 2000, vol. 165, No. 12, 6908-6914.
Leach et al. "Enhancement of Antitumor Immunity by CTLA-4 Blockade," Science, 1996, vol. 271, No. , pp. 1734-1736.
Peach et al. "Both Extracellular Immunoglobin-like Domains of CD80 Contain Residues Critical for Binding T Cell Surface Receptors CTLA-4 and CD28," Journal of Biological Chemistry, Sep. 1995, vol. 270, No. 36, pp. 21181-21187.
Peggs et al. "Cell intrinsic mechanisms of T-cell inhibition and application to cancer therapy," Immunological Reviews, Aug. 2008, vol. 224, No. 1, pp. 141-165.
Search Report for United Kingdom Patent Application No. GB1311475.6, dated Feb. 13, 2014, 4 pages.
International Search Report and Written Opinion for International (PCT) Patent Application No. PCT/EP2014/063442, dated Oct. 10, 2014, 12 pages.
International Preliminary Report on Patentability for International (PCT) Patent Application No. PCT/EP2014/063442, dated Dec. 29, 2015, 7 pages.
Altschul et al. "Basic Local Alignment Search Tool," J Mol Biol., 1990, vol. 215, No. 3, pp. 403-410.
Altschul "A Protein Alignment Scoring System Sensitive at All Evolutionary Distances," Journal of Molecular Evolution, 1993, vol. 36, No. 3, pp. 290-300.
Bauminger et al. "The Use of Carbodiimides in the Preparation of Immunizing Conjugates," Methods in Enzymology, 1980, vol. 70, pp. 151-159.
Caceci et al. "Fitting Curves to Data," BYTE, May 1984, vol. 9, No. 5, pp. 340-362.
Cornish-Bowden "Nomenclature for incompletely specified bases in nucleic acid sequences: recommendations 1984," Nucleic Acids Research, 1985, vol. 13, No. 9, pp. 3021-3030.
Devereux et al. "A comprehensive set of sequence analysis programs for the VAX," Nucleic Acids Research, 1984, vol. 12, No. 1, pp. 387-395.
Henikoff et al. "Amino acid substitution matrices from protein blocks," Proc. Natl. Acad. Sci. USA, Nov. 1992, vol. 89, No. 22, pp. 10915-10919.

(Continued)

Primary Examiner — Julie Ha
Assistant Examiner — Li Ni Komatsu
(74) Attorney, Agent, or Firm — Sheridan Ross P.C.

(57) ABSTRACT

The invention provides a polypeptide that specifically binds to CTLA-4, particularly human CTLA-4.

6 Claims, 5 Drawing Sheets

(56) References Cited

OTHER PUBLICATIONS

Karlin et al. "Applications and statistics for multiple high-scoring segmentts in molecular sequences," Proc. Natl. Acad. Sci. USA, Jun. 1993, vol. 90, No. 12, pp. 5873-5877.
Nomenclature Committee of the International Union of Biochemistry (NC-IUB) "Nomenclature for incompletely specified bases in nucleic acid sequences: Recommendations 1984," Eur. J. Biochem., 1985, vol. 150, pp. 1-5.
Wong et al. "A double-filter method for nitrocellulose-filter binding: Application to protein-nucleic acid interactions," Proc. Natl. Acad. Sci. USA, Jun. 1993, vol. 90, No. 12, pp. 5428-5432.
Nomenclature Committee of the International Union of Biochemistry (NC-IUB) "Nomenclature for incompletely specified bases in nucleic acid sequences: Recommendations 1984," Biochem. J., 1985, vol. 229, No. 2, pp. 281-286.
Nomenclature Committee of the International Union of Biochemistry (NC-IUB) "Nomenclature for incompletely specified bases in nucleic acid sequences: Recommendations 1984," Proc. Natl. Acad. Sci. USA, 1986, vol. 83, pp. 4-8 (reprinted from Eur. J. Biochem. 150, -15 (1985)).
Nomenclature Committee of the International Union of Biochemistry (NC-IUB) "Nomenclature for incompletely specified bases in nucleic acid sequences: Recommendations 1984," The Journal of Biological Chemistry, Jan. 1986, vol. 261, No. 1, pp. 13-17 (reproduced from Eur. J. Biochem. 150, -15 (1985)).
Nomenclature Committee of the International Union of Biochemistry (NC-IUB) "Nomenclature for incompletely specified bases in nucleic acid sequences: Recommendations 1984," Mol. Biol. Evol. 1986, vol. 3, No. 2, pp. 99-108 (reprinted from Eur. J. Biochem. 150, -15 (1985)).

\* cited by examiner

```
                                        24
                                        |
                          APLKIQA YFNETADLPC QFANSQNQSL SELVVFWQDQ      60
ENLVLNEVYL GKEKFDSVHS KYMGRTSFDS DSWTLRLHNL QIKDKGLYQC IIHHKKPTGM      120
IRIHQMNSEL SVLA                                                       134
```

B

```
MDPQCTMGLS NILFVMAFLL SGAAPLKIQA YFNETADLPC QFANSQNQSL SELVVFWQDQ      60
ENLVLNEVYL GKEKFDSVHS KYMGRTSFDS DSWTLRLHNL QIKDKGLYQC IIHHKKPTGM      120
IRIHQMNSEL SVLANFSQPE IVPISNITEN VYINLTCSSI HGYPEPKKMS VLLRTKNSTI      180
EYDGIMQKSQ DNVTELYDVS ISLSVSFPDV TSNMTIFCIL ETDKTRLLSS PFSIELEDPQ      240
PPPDHIP                                                               247
```

C

```
MDPQCTMGLS NILFVMAFLL SGAAPLKIQA YFNETADLPC QFANSQNQSL SELVVFWQDQ      60
ENLVLNEVYL GKEKFDSVHS KYMGRTSFDS DSWTLRLHNL QIKDKGLYQC IIHHKKPTGM      120
IRIHQMNSEL SVLANFSQPE IVPISNITEN VYINLTCSSI HGYPEPKKMS VLLRTKNSTI      180
EYDGIMQKSQ DNVTELYDVS ISLSVSFPDV TSNMTIFCIL ETDKTRLLSS PFSIELEDPQ      240
PPPDHIPWIT AVLPTVIICV MVFCLILWKW KKKKRPRNSY KCGTNTMERE ESEQTKKREK      300
IHIPERSDEA QRVFKSSKTS SCDKSDTCF
```

SEQUENCE LISTING

<160> NUMBER OF SEQ ID NOS: 46

<210> SEQ ID NO 1
<211> LENGTH: 137
<212> TYPE: PRT
<213> ORGANISM: Homo Sapiens

<400> SEQUENCE: 1

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Ala Lys Glu Lys Lys Pro Ser Tyr Asn Arg Gly Leu Cys
        115                 120                 125

Glu Asn Ala Pro Asn Arg Ala Arg Met
    130                 135

<210> SEQ ID NO 2
<211> LENGTH: 220
<212> TYPE: PRT
<213> ORGANISM: Homo Sapiens

<400> SEQUENCE: 2

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met 180                 185                 190
Asn Met Thr Pro Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 3
<211> LENGTH: 111
<212> TYPE: PRT
<213> ORGANISM: Homo Sapiens

<400> SEQUENCE: 3

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala
            100                 105                 110

<210> SEQ ID NO 4
<211> LENGTH: 247
<212> TYPE: PRT
<213> ORGANISM: Homo Sapiens

<400> SEQUENCE: 4

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn

```
                180                 185                 190
Val Thr Glu Leu Tyr Asp Val Ser Ile Ser Leu Ser Val Ser Phe Pro
            195                 200                 205

Asp Val Thr Ser Asn Met Thr Ile Phe Cys Ile Leu Glu Thr Asp Lys
        210                 215                 220

Thr Arg Leu Leu Ser Ser Pro Phe Ser Ile Glu Leu Glu Asp Pro Gln
225                 230                 235                 240

Pro Pro Pro Asp His Ile Pro
                245

<210> SEQ ID NO 5
<211> LENGTH: 111
<212> TYPE: PRT
<213> ORGANISM: Homo Sapiens

<400> SEQUENCE: 5

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val Ala Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His Lys Lys Pro Thr Gly
                85                  90                  95

Met Ile Arg Ile His Gln Met Asn Ser Glu Leu Ser Val Leu Ala
            100                 105                 110

<210> SEQ ID NO 6
<211> LENGTH: 109
<212> TYPE: PRT
<213> ORGANISM: Artificial Sequence
<220> FEATURE:
<223> OTHER INFORMATION: Synthetic construct clone number 900

<400> SEQUENCE: 6

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val Asp Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Val Ile His Lys Lys Pro Ser Gly Leu Val
                85                  90                  95

Lys Ile His Glu Met Asn Ser Glu Leu Ser Val Leu Ala
            100                 105

<210> SEQ ID NO 7
<211> LENGTH: 109
<212> TYPE: PRT
<213> ORGANISM: Artificial Sequence
```

<220> FEATURE:
<223> OTHER INFORMATION: Synthetic construct clone number 901

<400> SEQUENCE: 7

```
Leu Lys Ile Gln Ala Tyr Phe Asn Glu Thr Ala Asp Leu Pro Cys Gln
1               5                   10                  15

Phe Ala Asn Ser Gln Asn Leu Thr Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val His Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Val Ile His His Lys Pro Thr Gly Met Ile
                85                  90                  95

Lys Ile His Glu Met Asn Ser Glu Leu Ser Val Leu Thr
            100                 105
```

<210> SEQ ID NO 8
<211> LENGTH: 109
<212> TYPE: PRT
<213> ORGANISM: Artificial Sequence
<220> FEATURE:
<223> OTHER INFORMATION: Synthetic construct clone number 904

<400> SEQUENCE: 8

```
Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Ile Val Phe Trp
            20                  25                  30

Gln Asp Gln Glu Asn Leu Val Leu Asn Glu Val Tyr Leu Gly Lys Glu
        35                  40                  45

Arg Phe Asp Ala Val Asp Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Ile Ile His His Lys Lys Pro Ser Gly Met Val
                85                  90                  95

Lys Ile His Gln Met Asp Ser Glu Leu Ser Val Leu Ala
            100                 105
```

<210> SEQ ID NO 9
<211> LENGTH: 109
<212> TYPE: PRT
<213> ORGANISM: Artificial Sequence
<220> FEATURE:
<223> OTHER INFORMATION: Synthetic construct clone number 906

<400> SEQUENCE: 9

```
Leu Lys Ile Gln Ala Tyr Ile Asn Glu Thr Ala Asp Leu Pro Cys Gln
1               5                   10                  15

Phe Ala Asn Ser Gln Asn Leu Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Arg Phe Asp Ser Val Asp Ser Lys Tyr Met Gly Arg Thr Ser Phe Asp
    50                  55                  60
```

```
Ser Asp Ser Trp Thr Leu Arg Leu His Asn Leu Gln Ile Lys Asp Lys
 65                  70                  75                  80

Gly Phe Tyr Gln Cys Ile Ile His His Lys Lys Pro Thr Gly Leu Val
                 85                  90                  95

Lys Ile His Glu Met Asn Ser Glu Leu Ser Val Leu Ala
                100                 105
```

<210> SEQ ID NO 10
<211> LENGTH: 109
<212> TYPE: PRT
<213> ORGANISM: Artificial Sequence
<220> FEATURE:
<223> OTHER INFORMATION: Synthetic construct clone number 907

<400> SEQUENCE: 10

```
Leu Lys Ile Gln Ala Tyr Phe Asn Glu Thr Ala Asp Leu Pro Cys Gln
  1               5                  10                  15

Phe Ala Asn Ser Gln Asn Gln Ser Leu Ser Glu Leu Val Val Phe Trp
                 20                  25                  30

Gln Asp Gln Glu Asn Leu Val Leu Asn Glu Val Tyr Leu Gly Lys Glu
             35                  40                  45

Lys Phe Asp Ser Val His Ser Lys Tyr Met Gly Arg Thr Ser Phe Asp
 50                  55                  60

Ser Asp Ser Trp Thr Leu Arg Leu His Asn Leu Gln Ile Lys Asp Lys
 65                  70                  75                  80

Gly Leu Tyr Gln Cys Ile Ile His His Lys Lys Pro Thr Gly Met Ile
                 85                  90                  95

Lys Ile His Glu Met Asn Ser Glu Leu Ser Val Leu Ala
                100                 105
```

<210> SEQ ID NO 11
<211> LENGTH: 109
<212> TYPE: PRT
<213> ORGANISM: Artificial Sequence
<220> FEATURE:
<223> OTHER INFORMATION: Synthetic construct clone number 908

<400> SEQUENCE: 11

```
Leu Lys Ile Gln Ala Tyr Phe Asn Glu Thr Ala Asp Leu Pro Cys Gln
  1               5                  10                  15

Phe Ala Asn Ser Gln Asn Gln Ser Leu Ser Glu Leu Val Val Phe Trp
                 20                  25                  30

Gln Asp Gln Glu Asn Leu Val Leu Asn Glu Val Tyr Leu Gly Lys Glu
             35                  40                  45

Lys Phe Asp Ser Val His Ser Lys Tyr Met Gly Arg Thr Ser Phe Asp
 50                  55                  60

Ser Asp Ser Trp Thr Leu Arg Leu His Asn Leu Gln Ile Lys Asp Lys
 65                  70                  75                  80

Gly Ile Tyr Gln Cys Ile Ile His His Lys Lys Pro Thr Gly Met Val
                 85                  90                  95

Lys Ile His Glu Met Asn Ser Glu Leu Ser Val Leu Ala
                100                 105
```

<210> SEQ ID NO 12
<211> LENGTH: 109
<212> TYPE: PRT
<213> ORGANISM: Artificial Sequence
<220> FEATURE:
<223> OTHER INFORMATION: Synthetic construct clone number 910

<400> SEQUENCE: 12

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
                20                  25                  30

Gln Asp Gln Glu Asn Leu Val Leu Asn Glu Val Tyr Leu Gly Lys Glu
            35                  40                  45

Lys Phe Asp Ser Val Asp Ser Lys Tyr Met Gly Arg Thr Ser Phe Asp
        50                  55                  60

Ser Asp Ser Trp Thr Leu Arg Leu His Asn Leu Gln Ile Lys Asp Lys
65                  70                  75                  80

Gly Ile Tyr Gln Cys Ile Ile His His Lys Lys Pro Thr Gly Met Val
                85                  90                  95

Lys Ile His Glu Met Asn Ser Glu Leu Ser Val Leu Ala
                100                 105

<210> SEQ ID NO 13
<211> LENGTH: 109
<212> TYPE: PRT
<213> ORGANISM: Artificial Sequence
<220> FEATURE:
<223> OTHER INFORMATION: Synthetic construct clone number 915

<400> SEQUENCE: 13

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
                20                  25                  30

Gln Asp Gln Glu Asn Leu Ile Leu Asn Glu Val Tyr Leu Gly Lys Glu
            35                  40                  45

Lys Phe Asp Ser Val Asp Ser Lys Tyr Met Gly Arg Thr Ser Phe Asp
        50                  55                  60

Ser Asp Ser Trp Thr Leu Arg Leu His Asn Leu Gln Ile Lys Asp Lys
65                  70                  75                  80

Gly Phe Tyr Gln Cys Ile Ile His His Lys Lys Pro Ser Gly Leu Ile
                85                  90                  95

Lys Ile His Gln Met Asp Ser Glu Leu Ser Val Leu Ala
                100                 105

<210> SEQ ID NO 14
<211> LENGTH: 109
<212> TYPE: PRT
<213> ORGANISM: Artificial Sequence
<220> FEATURE:
<223> OTHER INFORMATION: Synthetic construct clone number 938

<400> SEQUENCE: 14

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
                20                  25                  30

Gln Asp Gln Glu Asn Leu Ile Leu Asn Glu Val Tyr Leu Gly Lys Glu
            35                  40                  45

Lys Phe Asp Ser Val His Ser Lys Tyr Met Gly Arg Thr Ser Phe Asp
        50                  55                  60

Ser Asp Ser Trp Thr Leu Arg Leu His Asn Leu Gln Ile Lys Asp Lys
65                  70                  75                  80

```
Gly Ile Tyr Gln Cys Ile Ile His His Lys Pro Thr Gly Met Val
                85                  90                  95

Lys Ile His Gln Met Asn Ser Glu Leu Ser Val Leu Ala
            100                 105
```

<210> SEQ ID NO 15
<211> LENGTH: 111
<212> TYPE: PRT
<213> ORGANISM: Artificial Sequence
<220> FEATURE:
<223> OTHER INFORMATION: Synthetic construct clone number 1038

<400> SEQUENCE: 15

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val Asp Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Pro Thr Gly
                85                  90                  95

Met Val Lys Ile His Glu Met Asn Ser Glu Leu Ser Val Leu Ala
            100                 105                 110
```

<210> SEQ ID NO 16
<211> LENGTH: 111
<212> TYPE: PRT
<213> ORGANISM: Artificial Sequence
<220> FEATURE:
<223> OTHER INFORMATION: Synthetic construct clone number 1039

<400> SEQUENCE: 16

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val Ser Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Pro Ser Gly
                85                  90                  95

Met Val Lys Ile His Gln Met Asp Ser Glu Leu Ser Val Leu Ala
            100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: Synthetic construct clone number 1040

<400> SEQUENCE: 17

Ala Pro Leu Lys Ile Gln Ala Tyr Phe Asn Glu Thr Ala Asp Leu Pro

```
                1               5                   10                  15
Cys Gln Phe Ala Asn Ser Gln Asn Leu Ser Leu Ser Glu Leu Val Val
                    20                  25                  30

Phe Trp Gln Asp Gln Glu Asn Leu Val Leu Asn Glu Val Tyr Leu Gly
            35                  40                  45

Lys Glu Arg Phe Asp Ser Val Asp Ser Lys Tyr Met Gly Arg Thr Ser
        50                  55                  60

Phe Asp Ser Asp Ser Trp Thr Leu Arg Leu His Asn Leu Gln Ile Lys
65                  70                  75                  80

Asp Lys Gly Arg Tyr Gln Cys Ile Ile His His Lys Lys Pro Thr Gly
                    85                  90                  95

Met Ile Asn Ile His Gln Met Asn Ser Glu Leu Ser Val Leu Ala
                100                 105                 110
```

<210> SEQ ID NO 18
<211> LENGTH: 111
<212> TYPE: PRT
<213> ORGANISM: Artificial Sequence
<220> FEATURE:
<223> OTHER INFORMATION: Synthetic construct clone number 1041

<400> SEQUENCE: 18

```
Ala Pro Leu Lys Ile Gln Ala Tyr Leu Asn Glu Thr Ala Asp Leu Pro
1               5                   10                  15

Cys Gln Phe Ala Asn Ser Gln Asn Leu Ser Leu Ser Glu Leu Val Val
                    20                  25                  30

Phe Trp Gln Asp Gln Glu Asn Leu Val Leu Asn Glu Val Tyr Leu Gly
            35                  40                  45

Lys Glu Lys Phe Asp Ser Val Asp Ser Lys Tyr Met Gly Arg Thr Ser
        50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Thr Gly
                    85                  90                  95

Leu Val Lys Ile His Glu Met Asn Ser Glu Leu Ser Val Leu Ala
                100                 105                 110
```

<210> SEQ ID NO 19
<211> LENGTH: 111
<212> TYPE: PRT
<213> ORGANISM: Artificial Sequence
<220> FEATURE:
<223> OTHER INFORMATION: Synthetic construct clone number 1042

<400> SEQUENCE: 19

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
                    20                  25                  30

Phe Trp Gln Asp Gln Glu Asn Leu Val Leu Asn Glu Val Tyr Leu Gly
            35                  40                  45

Lys Glu Ile Phe Asp Ser Val Ser Ser Lys Tyr Met Gly Arg Thr Ser
        50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Ser Gly
                    85                  90                  95
```

```
Met Val Lys Ile His Gln Met Asp Ser Glu Leu Ser Val Leu Ala
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: Synthetic construct clone number 1043

<400> SEQUENCE: 20

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val Asp Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Thr Gly
                85                  90                  95

Met Ile Lys Ile His Glu Met Asn Ser Glu Leu Ser Val Leu Ala
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: Synthetic construct clone number 1044

<400> SEQUENCE: 21

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Thr Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val Ser Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Thr Gly
                85                  90                  95

Met Ile Lys Ile His Glu Met Ser Ser Glu Leu Ser Val Leu Ala
            100                 105                 110
```

<210> SEQ ID NO 22
<211> LENGTH: 111
<212> TYPE: PRT
<213> ORGANISM: Artificial Sequence
<220> FEATURE:
<223> OTHER INFORMATION: Synthetic construct clone number 1045

<400> SEQUENCE: 22

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Thr Leu Ser Glu Leu Val Val
```

```
                    20                  25                  30

Phe Trp Gln Asp Gln Glu Asn Leu Val Leu Asn Glu Val Tyr Leu Gly
                35                  40                  45

Lys Glu Lys Phe Asp Ser Val Asp Ser Lys Tyr Met Gly Arg Thr Ser
         50                  55                  60

Phe Asp Ser Asp Ser Trp Thr Leu Arg Leu His Asn Leu Gln Ile Lys
 65                  70                  75                  80

Asp Lys Gly Leu Tyr Gln Cys Ile Ile His His Lys Lys Pro Thr Gly
                85                  90                  95

Leu Val Lys Ile His Glu Met Asn Ser Glu Leu Ser Val Leu Ala
                100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Synthetic construct clone number 1046

<400> SEQUENCE: 23

Ala Pro Leu Lys Ile Gln Ala Tyr Phe Asn Glu Thr Ala Asp Leu Pro
 1               5                  10                  15

Cys Gln Phe Ala Asn Ser Gln Asn Gln Ser Leu Ser Glu Leu Val Val
                20                  25                  30

Phe Trp Gln Asp Gln Glu Asn Leu Val Leu Asn Glu Val Tyr Leu Gly
                35                  40                  45

Lys Glu Lys Phe Asp Ser Val Asp Ser Lys Tyr Met Gly Arg Thr Ser
         50                  55                  60

Phe Asp Ser Asp Ser Trp Thr Leu Arg Leu His Asn Leu Gln Ile Glu
 65                  70                  75                  80

Asp Lys Gly Ile Tyr Gln Cys Ile Ile His His Lys Lys Pro Ser Gly
                85                  90                  95

Met Val Lys Ile His Gln Met Asp Ser Glu Leu Ser Val Leu Ala
                100                 105                 110

<210> SEQ ID NO 24
<211> LENGTH: 111
<212> TYPE: PRT
<213> ORGANISM: Artificial Sequence
<220> FEATURE:
<223> OTHER INFORMATION: Synthetic construct clone number 1047

<400> SEQUENCE: 24

Ala Pro Leu Lys Ile Gln Ala Tyr Phe Asn Glu Thr Ala Asp Leu Pro
 1               5                  10                  15

Cys Gln Phe Ala Asn Ser Gln Asn Leu Ser Leu Ser Glu Leu Val Val
                20                  25                  30

Phe Trp Gln Asp Gln Glu Asn Leu Val Leu Asn Glu Val Tyr Leu Gly
                35                  40                  45

Lys Glu Lys Phe Asp Ser Val Asp Ser Lys Tyr Met Gly Arg Thr Ser
         50                  55                  60

Phe Asp Ser Asp Ser Trp Thr Leu Arg Leu His Asn Leu Gln Ile Lys
 65                  70                  75                  80

Asp Lys Gly Ile Tyr Gln Cys Ile Ile His His Lys Lys Pro Thr Gly
                85                  90                  95

Leu Val Lys Ile His Glu Met Asn Ser Glu Leu Ser Val Leu Ala
                100                 105                 110
```

<210> SEQ ID NO 25
<211> LENGTH: 327
<212> TYPE: DNA
<213> ORGANISM: Artificial Sequence
<220> FEATURE:
<223> OTHER INFORMATION: Synthetic construct of clone number 900

<400> SEQUENCE: 25
ctcaaaatcc aagcgtactt caacgaaact gcagacttac cgtgtcagtt tgccaattcg    60
cagaatcaaa gcctgagcga actggtggtt ttctggcagg atcaggagaa cctggttctg   120
aacgaagtct atctgggcaa agagaaattc gacagcgtgg acagcaagta tatgggccgc   180
accagctttg atagcgacag ctggaccctg cgtctgcaca atctgcaaat caaagataag   240
ggtatctacc agtgcgtgat ccaccataag aagccgagcg gtctggtgaa gattcacgag   300
atgaactccg agttgtctgt cctggcg                                       327

<210> SEQ ID NO 26
<211> LENGTH: 327
<212> TYPE: DNA
<213> ORGANISM: Artificial Sequence
<220> FEATURE:
<223> OTHER INFORMATION: Synthetic construct of clone number 901

<400> SEQUENCE: 26
ctcaaaatcc aagcgtactt caacgaaact gcagacttac cgtgtcagtt tgccaattcg    60
cagaatctga ccctgagcga actggtggtt ttctggcagg atcaggagaa cctggttctg   120
aacgaagtct atctgggcaa agagaaattc gacagcgtgc atagcaagta tatgggccgc   180
accagctttg atagcgacag ctggaccctg cgtctgcaca atctgcaaat caaagataag   240
ggtatctacc agtgcgtgat ccaccataag aagccgacgg tatgattaa gattcacgag    300 atgaactccg agttgtctgt cctgacc                                       327

<210> SEQ ID NO 27
<211> LENGTH: 327
<212> TYPE: DNA
<213> ORGANISM: Artificial Sequence
<220> FEATURE:
<223> OTHER INFORMATION: Synthetic construct of clone number 904

<400> SEQUENCE: 27
ctcaaaatcc aagcgtactt caacgaaact gcagacttac cgtgtcagtt tgccaattcg    60
cagaatcaaa gcctgagcga actgatcgtt ttctggcagg atcaggagaa cctggttctg   120
aacgaagtct atctgggcaa agagcggttc gacgccgtgg acagcaagta tatgggccgc   180
accagctttg atagcgacag ctggaccctg cgtctgcaca atctgcaaat caaagataag   240
ggtatctacc agtgcattat ccaccataag aagccgagcg gtatggtgaa gattcaccaa   300
atggactccg agttgtctgt cctggcg                                       327

<210> SEQ ID NO 28
<211> LENGTH: 327
<212> TYPE: DNA
<213> ORGANISM: Artificial Sequence
<220> FEATURE:
<223> OTHER INFORMATION: Synthetic construct of clone number 906

<400> SEQUENCE: 28
ctcaaaatcc aagcgtacat caacgaaact gcagacttac cgtgtcagtt tgccaattcg    60
cagaatctga gcctgagcga actggtggtt ttctggcagg atcaggagaa cctggttctg   120

```
aacgaagtct atctgggcaa agagcggttc gacagcgtgg acagcaagta tatgggccgc    180
accagctttg atagcgacag ctggaccctg cgtctgcaca atctgcaaat caaagataag    240
ggtttctacc agtgcattat ccaccataag aagccgacgg gtctggtgaa gattcacgag    300
atgaactccg agttgtctgt cctggcg                                       327
```

<210> SEQ ID NO 29
<211> LENGTH: 327
<212> TYPE: DNA
<213> ORGANISM: Artificial Sequence
<220> FEATURE:
<223> OTHER INFORMATION: Synthetic construct of clone number 907

<400> SEQUENCE: 29

```
ctcaaaatcc aagcgtactt caacgaaact gcagacttac cgtgtcagtt tgccaattcg     60
cagaatcaaa gcctgagcga actggtggtt ttctggcagg atcaggagaa cctggttctg    120
aacgaagtct atctgggcaa agagaaattc gacagcgtgc atagcaagta tatgggccgc    180
accagctttg atagcgacag ctggaccctg cgtctgcaca atctgcaaat caaagataag    240
ggtctgtacc agtgcattat ccaccataag aagccgacgg gtatgattaa gattcacgag    300
atgaactccg agttgtctgt cctggcg                                       327
```

<210> SEQ ID NO 30
<211> LENGTH: 327
<212> TYPE: DNA
<213> ORGANISM: Artificial Sequence
<220> FEATURE:
<223> OTHER INFORMATION: Synthetic construct of clone number 908

<400> SEQUENCE: 30

```
ctcaaaatcc aagcgtactt caacgaaact gcagacttac cgtgtcagtt tgccaattcg     60
cagaatcaaa gcctgagcga actggtggtt ttctggcagg atcaggagaa cctggttctg    120
aacgaagtct atctgggcaa agagaaattc gacagcgtgc atagcaagta tatgggccgc    180
accagctttg atagcgacag ctggaccctg cgtctgcaca atctgcaaat caaagataag    240
ggtatctacc agtgcattat ccaccataag aagccgacgg gtatggtgaa gattcacgag    300
atgaactccg agttgtctgt cctggcg                                       327
```

<210> SEQ ID NO 31
<211> LENGTH: 327
<212> TYPE: DNA
<213> ORGANISM: Artificial Sequence
<220> FEATURE:
<223> OTHER INFORMATION: Synthetic construct of clone number 910

<400> SEQUENCE: 31

```
ctcaaaatcc aagcgtactt caacgaaact gcagacttac cgtgtcagtt tgccaattcg     60
cagaatcaaa gcctgagcga actggtggtt ttctggcagg atcaggagaa cctggttctg    120
aacgaagtct atctgggcaa agagaaattc gacagcgtgg acagcaagta tatgggccgc    180
accagctttg atagcgacag ctggaccctg cgtctgcaca atctgcaaat caaagataag    240
ggtatctacc agtgcattat ccaccataag aagccgacgg gtatggtgaa gattcacgag    300
atgaactccg agttgtctgt cctggcg                                       327
```

<210> SEQ ID NO 32
<211> LENGTH: 327
<212> TYPE: DNA

<213> ORGANISM: Artificial Sequence
<220> FEATURE:
<223> OTHER INFORMATION: Synthetic construct of clone number 915

<400> SEQUENCE: 32

| | |
|---|---|
| ctcaaaatcc aagcgtactt caacgaaact gcagacttac cgtgtcagtt tgccaattcg | 60 |
| cagaatcaaa gcctgagcga actggtggtt ttctggcagg atcaggagaa cctgatcctg | 120 |
| aacgaagtct atctgggcaa agagaaattc gacagcgtgg acagcaagta tatgggccgc | 180 |
| accagctttg atagcgacag ctggaccctg cgtctgcaca atctgcaaat caaagataag | 240 |
| ggtttctacc agtgcattat ccaccataag aagccgagcg gtctgattaa gattcaccaa | 300 |
| atggactccg agttgtctgt cctggcg | 327 |

<210> SEQ ID NO 33
<211> LENGTH: 327
<212> TYPE: DNA
<213> ORGANISM: Artificial Sequence
<220> FEATURE:
<223> OTHER INFORMATION: Synthetic construct of clone number 938

<400> SEQUENCE: 33

| | |
|---|---|
| ctcaaaatcc aagcgtactt caacgaaact gcagacttac cgtgtcagtt tgccaattcg | 60 |
| cagaatctga gcctgagcga actggtggtt ttctggcagg atcaggagaa cctgatcctg | 120 |
| aacgaagtct atctgggcaa agagcggttc gacagcgtgc atagcaagta tatgggccgc | 180 |
| accagctttg atagcgacag ctggaccctg cgtctgcaca atctgcaaat caaagataag | 240 |
| ggtctgtacc agtgcattat ccaccataag aagccgagcg gtatggtgaa gattcacgag | 300 |
| atgaactccg agttgtctgt cctggcg | 327 |

<210> SEQ ID NO 34
<211> LENGTH: 333
<212> TYPE: DNA
<213> ORGANISM: Artificial Sequence
<220> FEATURE:
<223> OTHER INFORMATION: Synthetic construct of clone number 1038

<400> SEQUENCE: 34

| | |
|---|---|
| gccccctca aaatccaagc gtacttcaac gaaactgcag acttaccgtg tcagtttgcc | 60 |
| aattcgcaga atctgagcct gagcgaactg gtggttttct ggcaggatca ggagaacctg | 120 |
| gttctgaacg aagtctatct gggcaaagag aaattcgaca gcgtggacag caagtatatg | 180 |
| ggccgcacca gctttgatag cgacagctgg accctgcgtc tgcacaatct gcaaatcaaa | 240 |
| gataagggta tctaccagtg cattatccac cataagaagc cgacgggtat ggtgaagatt | 300 |
| cacgagatga actccgagtt gtctgtcctg gcg | 333 |

<210> SEQ ID NO 35
<211> LENGTH: 333
<212> TYPE: DNA
<213> ORGANISM: Artificial Sequence
<220> FEATURE:
<223> OTHER INFORMATION: Synthetic construct of clone number 1039

<400> SEQUENCE: 35

| | |
|---|---|
| gccccctca aaatccaagc gtacttcaac gaaactgcag acttaccgtg tcagtttgcc | 60 |
| aattcgcaga atctgagcct gagcgaactg gtggttttct ggcaggatca ggagaacctg | 120 |
| gttctgaacg aagtctatct gggcaaagag aaattcgaca gcgtgagtag caagtatatg | 180 |
| ggccgcacca gctttgatag cgacagctgg accctgcgtc tgcacaatct gcaaatcaaa | 240 |

```
gataagggta tctaccagtg cattatccac cataagaagc cgagcggtat ggtgaagatt    300
caccaaatgg actccgagtt gtctgtcctg gcg                                 333
```

<210> SEQ ID NO 36
<211> LENGTH: 333
<212> TYPE: DNA
<213> ORGANISM: Artificial Sequence
<220> FEATURE:
<223> OTHER INFORMATION: Synthetic construct of clone number 1040

<400> SEQUENCE: 36

```
gcccccctca aaatccaagc gtacttcaac gaaactgcag acttaccgtg tcagtttgcc     60
aattcgcaga atctgagcct gagcgaactg gtggttttct ggcaggatca ggagaacctg    120
gttctgaacg aagtctatct gggcaaagag cggttcgaca gcgtggacag caagtatatg    180
ggccgcacca gctttgatag cgacagctgg accctgcgtc tgcacaatct gcaaatcaaa    240
gataagggta ggtaccagtg cattatccac cataagaagc cgacgggtat gattaatatt    300
caccaaatga actccgagtt gtctgtcctg gcg                                 333
```

<210> SEQ ID NO 37
<211> LENGTH: 333
<212> TYPE: DNA
<213> ORGANISM: Artificial Sequence
<220> FEATURE:
<223> OTHER INFORMATION: Synthetic construct of clone number 1041

<400> SEQUENCE: 37

```
gcccccctca aaatccaagc gtacctcaac gaaactgcag acttaccgtg tcagtttgcc     60
aattcgcaga atctgagcct gagcgaactg gtggttttct ggcaggatca ggagaacctg    120
gttctgaacg aagtctatct gggcaaagag aaattcgaca gcgtggacag caagtatatg    180
ggccgcacca gctttgatag cgacagctgg accctgcgtc tgcacaatct gcaaatcaaa    240
gataagggta tctaccagtg cattatccac cataagaagc cgacgggtct ggtgaagatt    300
cacgagatga actccgagtt gtctgtcctg gcg                                 333
```

<210> SEQ ID NO 38
<211> LENGTH: 333
<212> TYPE: DNA
<213> ORGANISM: Artificial Sequence
<220> FEATURE:
<223> OTHER INFORMATION: Synthetic construct of clone number 1042

<400> SEQUENCE: 38

```
gcccccctca aaatccaagc gtacttcaac gaaactgcag acttaccgtg tcagtttgcc     60
aattcgcaga atctgagcct gagcgaactg gtggttttct ggcaggatca ggagaacctg    120
gttctgaacg aagtctatct gggcaaagag attttcgaca gcgtgagtag caagtatatg    180
ggccgcacca gctttgatag tgacagctgg accctgcgtc tgcacaatct gcaaatcaaa    240
gataagggta tctaccagtg cattatccac cataagaagc cgagcggtat ggtgaagatt    300
caccaaatgg actccgagtt gtctgtcctg gcg                                 333
```

<210> SEQ ID NO 39
<211> LENGTH: 333
<212> TYPE: DNA
<213> ORGANISM: Artificial Sequence
<220> FEATURE:
<223> OTHER INFORMATION: Synthetic construct of clone number 1043

<400> SEQUENCE: 39

```
gccccccctca aaatccaagc gtacttcaac gaaactgcag acttaccgtg tcagtttgcc      60
aattcgcaga atctgagcct gagcgaactg gtggttttct ggcaggatca ggagaacctg     120
gttctgaacg aagtctatct gggcaaagag aaattcgaca gcgtggatag caagtatatg     180
ggccgcacca gctttgatag cgacagctgg accctgcgtc tgcacaatct gcaaatcaaa     240
gataagggta tctaccagtg cattatccac cataagaagc cgacgggtat gattaagatt     300
cacgagatga actccgagtt gtctgtcctg gcg                                   333
```

<210> SEQ ID NO 40
<211> LENGTH: 333
<212> TYPE: DNA
<213> ORGANISM: Artificial Sequence
<220> FEATURE:
<223> OTHER INFORMATION: Synthetic construct of clone number 1044

<400> SEQUENCE: 40

```
gccccccctca aaatccaagc gtacttcaac gaaactgcag acttaccgtg tcagtttgcc      60
aattcgcaga atctgaccct gagcgaactg gtggttttct ggcaggatca ggagaacctg     120
gttctgaacg aagtctatct gggcaaagag aaattcgaca gcgtgtctag caagtatatg     180
ggccgcacca gctttgatag cgacagctgg accctgcgtc tgcacaatct gcaaatcaaa     240
gataagggta tctaccagtg cattatccac cataagaagc cgacgggtat gattaagatt     300
cacgagatga gctccgagtt gtctgtcctg gcg                                   333
```

<210> SEQ ID NO 41
<211> LENGTH: 333
<212> TYPE: DNA
<213> ORGANISM: Artificial Sequence
<220> FEATURE:
<223> OTHER INFORMATION: Synthetic construct of clone number 1045

<400> SEQUENCE: 41

```
gccccccctca aaatccaagc gtacttcaac gaaactgcag acttaccgtg tcagtttgcc      60
aattcgcaga atctgaccct gagcgaactg gtggttttct ggcaggatca ggagaacctg     120
gttctgaacg aagtctatct gggcaaagag aaattcgaca gcgtggacag caagtatatg     180
ggccgcacca gctttgatag cgacagctgg accctgcgtc tgcacaatct gcaaatcaaa     240
gataagggtc tgtaccagtg cattatccac cataagaagc cgacgggtct ggtgaagatt     300
cacgagatga actccgagtt gtctgtcctg gcg                                   333
```

<210> SEQ ID NO 42
<211> LENGTH: 333
<212> TYPE: DNA
<213> ORGANISM: Artificial Sequence
<220> FEATURE:
<223> OTHER INFORMATION: Synthetic construct of clone number 1046

<400> SEQUENCE: 42

```
gccccccctca aaatccaagc gtacttcaac gaaactgcag acttaccgtg tcagtttgcc      60
aattcgcaga atcaaagcct gagcgaactg gtggttttct ggcaggatca ggagaacctg     120
gttctgaacg aagtctatct gggcaaagag aaattcgaca gcgtggacag caagtatatg     180
ggccgcacca gctttgatag cgacagctgg accctgcgtc tgcacaatct gcaaatcgaa     240
gataagggta tctaccagtg cattatccac cataagaagc cgagcggtat ggtgaagatt     300
caccaaatgg actccgagtt gtctgtcctg gcg                                   333
```

<210> SEQ ID NO 43
<211> LENGTH: 333
<212> TYPE: DNA
<213> ORGANISM: Artificial Sequence
<220> FEATURE:
<223> OTHER INFORMATION: Synthetic construct of clone number 1047

<400> SEQUENCE: 43

```
gccccctca aaatccaagc gtacttcaac gaaactgcag acttaccgtg tcagtttgcc      60
aattcgcaga atctgagcct gagcgaactg gtggttttct ggcaggatca ggagaacctg    120
gttctgaacg aagtctatct gggcaaagag aaattcgaca gcgtggacag caagtatatg    180
ggccgcacca gctttgatag cgacagctgg accctgcgtc tgcacaatct gcaaatcaaa    240
gataagggta tctaccagtg cattatccac cataagaagc cgacgggtct ggtgaagatt    300
cacgagatga actccgagtt gtctgtcctg gcg                                 333
```

<210> SEQ ID NO 44
<211> LENGTH: 329
<212> TYPE: PRT
<213> ORGANISM: Homo Sapiens

<400> SEQUENCE: 44

```
Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255
```

```
Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```

<210> SEQ ID NO 45
<211> LENGTH: 223
<212> TYPE: PRT
<213> ORGANISM: Mus musculus

<400> SEQUENCE: 45

```
Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Ser Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 46
<211> LENGTH: 218
<212> TYPE: PRT
<213> ORGANISM: Mus musculus

<400> SEQUENCE: 46

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30
```

-continued

```
Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Val Thr Thr Met Asn Met
            180                 185                 190

Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
    210                 215
```

US 9,834,589 B2

CD86 VARIANTS WITH IMPROVED AFFINITY FOR CTLA-4

CROSS REFERENCE TO RELATED APPLICATIONS

This application is a national stage application under 35 U.S.C. 371 and claims the benefit of PCT Application No. PCT/EP2014/063442 having an international filing date of Jun. 25, 2014, which designated the U.S., which PCT application claimed the benefit of Great Britain Patent Application No. 1311475.6 filed Jun. 27, 2013, the disclosures of which are incorporated herein by reference.

REFERENCE TO SEQUENCE LISTING

This application contains a Sequence Listing submitted as an electronic text file named "8275AB-1_Sequence_Listing_ST25.txt", having a size in bytes of 45 kb, and created on Dec. 9, 2015, and corrected for minor typographical issues in identifier codes and descriptions only, as submitted to the US Patent Office as an electronic text file on Jun. 30, 2016, having a size in bytes of 46 kb. The information contained in the electronic file(s) is hereby incorporated by reference in its entirety pursuant to 37 CFR §1.52(e)(5).

FIELD OF THE INVENTION

The present invention relates to polypeptides that specifically bind to CTLA-4, and in particular to human CTLA-4.

BACKGROUND TO THE INVENTION

Cancer is a leading cause of premature deaths in the developed world. The aim of immunotherapy in cancer is to mount an effective immune response by the body against a tumour. The key effector cell of a long lasting anti-tumor immune response is the activated tumor specific effector T cell. Cancer patients usually have T-cells specific for tumor antigens, however, the activity of these T-cells is frequently suppressed by inhibitory factors and pathways in the tumor micro-environment. Accordingly, there exists a need for methods for preventing or treating cancer which augment the T cell anti-tumour response.

SUMMARY OF THE INVENTION

The T cell anti-tumour response may be augmented by increasing T cell activation. T cell activation is triggered by the T cell receptor recognizing antigenic peptide presented by the MHC complex. There are then a number of checkpoints which regulate T cell activation. For example, the T cell receptor CTLA-4 serves as a negative regulator of T cell activation, and is upregulated on the T-cell surface following initial activation. The ligands of the CTLA-4 receptor are the B7 proteins (B7-1 and B7-2), which are expressed by antigen presenting cells. The corresponding receptor responsible for the upregulation of T cell activation is CD28, which competes for binding to the B7 proteins with CTLA-4. Thus, by blocking the CTLA-4 interaction with the B7 proteins, but not the CD28 interaction with the B7 proteins, one of the normal check points of the immune response may be removed, leading to augmented anti-tumour T cell responses.

The present inventors have produced and isolated novel polypeptides derived from the extracellular domain of human B7-2 polypeptide (CD86). The wild-type amino acid sequence of the extracellular domain of human CD86 (without signal sequence) is shown in SEQ ID NO: 3. This wild type sequence may optionally lack Alanine and Proline at the N terminus, that is positions 24 and 25. These amino acids may be referred to herein as A24 and P25 respectively. The wild-type amino acid sequence of the extracellular domain of human CD86 including signal sequence is shown in SEQ ID NO: 4. The wild-type amino acid sequence of full length human CD86 is shown in SEQ ID NO: 44.

The present invention provides a polypeptide comprising or consisting of an amino acid sequence in which at least one amino acid is changed when compared to the amino acid sequence of SEQ ID NO: 3, or said sequence lacking A24 and P25, wherein said polypeptide binds to CTLA-4 with higher affinity than wild-type CD86.

The polypeptide of the invention may have a binding strength ratio for CTLA-4 versus CD28 which is higher than the corresponding binding strength ratio of wild-type human CD86. The polypeptide may optionally bind to human CD28 with lower affinity than wild-type human CD86.

Also provided is a polypeptide of the invention for use in a method of treating or preventing a disease or condition in an individual.

Also provided is a method of treating a disease or condition in an individual, the method comprising administering to said individual a polypeptide according to the invention and thereby treating the disease or condition.

Also provided is a polypeptide of the invention for use in the manufacture of a medicament for treating a disease or condition in an individual.

Also provided is a method of increasing the activation of a cell expressing CTLA-4, optionally human or murine CTLA-4, the method comprising administering to said cell a polypeptide of the invention, optionally wherein said cell is a T cell.

Also provided is a polynucleotide encoding a polypeptide of the invention, and a vector or cell comprising a said polynucleotide. Also provided is a method of producing a polypeptide of the invention, comprising expressing a said polynucleotide in a cell.

Also provided is a method of identifying a CTLA-4 binding polypeptide, comprising determining whether or not a candidate polypeptide competes for binding to CTLA-4, optionally human or murine CTLA-4. with a polypeptide of the invention, wherein the candidate polypeptide does not comprise an amino acid sequence which is identical to SEQ ID NO: 3.

BRIEF DESCRIPTION OF THE SEQUENCE LISTING

SEQ ID NO: 1 is the amino acid sequence of human CTLA-4 (corresponding to GenBank: AAD00698.1)

SEQ ID NO: 2 is the amino acid sequence of human CD28 (corresponding to GenBank: AAA51944.1)

SEQ ID NO: 3 is the amino acid sequence of the monomeric extracellular domain of human wildtype CD86, excluding a 23 amino acid signal sequence from the N terminus.

SEQ ID NO: 4 is the amino acid sequence of the monomeric extracellular and transmembrane domains of human wildtype CD86, including N-terminal signal sequence. All numbering of amino acid positions herein is based on the positions in SEQ ID NO: 4 starting from the N terminus. Thus, the Alanine at the N terminus of SEQ ID NO: 3 is numbered 24.

SEQ ID NO: 5 is the amino acid sequence of a mutant form of the extracellular domain of human CD86 disclosed in Peach et at (Journal of Biological Chemistry 1995, vol 270(36), 21181-21187). H at position 79 of the wild type sequence is substituted with A in the corresponding position for the sequence of SEQ ID NO: 5. This change is referred to herein as H79A. Equivalent nomenclature is used throughout for other amino acid substitutions referred to herein. Numbering of positions is based on SEQ ID NO: 4 as outlined above.

SEQ ID NOs: 6 to 24 are the amino acid sequences of specific proteins of the invention.

SEQ ID NOs: 25 to 43 are nucleotide sequences encoding the amino acid sequences of each of SEQ ID NOs 6 to 24, respectively SEQ ID NO: 44 is the the full length amino acid sequence of human CD86 (corresponding to GenBank: ABK41931.1)

SEQ ID NO: 45 is the amino acid sequence of murine CTLA-4 (corresponding to UniProtKB/Swiss-Prot: P09793.1)

SEQ ID NO: 46 is the amino acid sequence of murine CD28 (corresponding to GenBank: AAA37395.1)

BRIEF DESCRIPTION OF THE FIGURES

FIG. 4 provides a schematic representation of human wild-type CD86 amino acid sequences disclosed herein. A is the amino acid sequence of the monomeric soluble extracellular domain of human CD86 without N-terminal signal sequence (SEQ ID NO: 3); B is the amino acid sequence of the monomeric extracellular and transmembrane domains of human wildtype CD86, including N-terminal signal sequence (SEQ ID NO: 4); C is the full length amino acid sequence of human CD86 (Genbank ABK41931.1; SEQ ID NO: 44). The sequence in A may optionally lack Alanine and Proline at the N terminus, that is positions 24 and 25, shown in bold. Signal sequences in B and C are underlined. Numbering of amino acid positions is based on SEQ ID NOs: 4 and 44, starting from the N terminus.

DETAILED DESCRIPTION OF THE INVENTION

Figure 1:
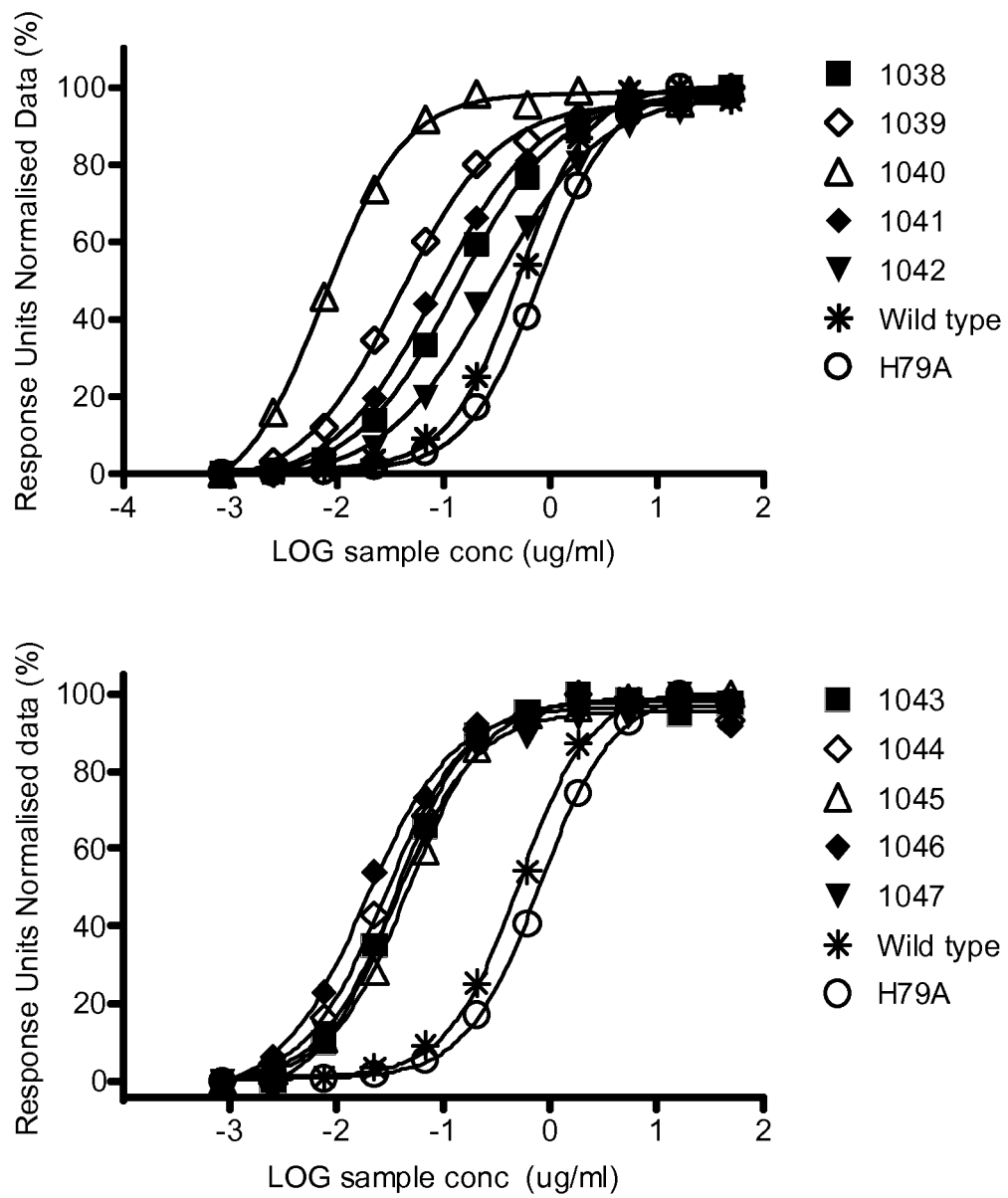
FIG. 1 shows the CTLA-4 binding properties of polypeptides of the invention as determined by an ELISA binding assay.

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an inhibitor" includes two or more such inhibitors, or reference to "an oligonucleotide" includes two or more such oligonucleotides and the like.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

All publications, patents and patent applications cited herein, whether supra or infra, are hereby incorporated by reference in their entirety.

The Human CD86 (B7-2) Polypeptide

The B7 proteins, CD80 and CD86 (B7-1 and B7-2), are expressed on the surface of antigen presenting cells and interact with the T cell receptors CD28 and CTLA-4. The binding of the B7 molecules to CD28 promotes T cell activation while binding of B7 molecules to CTLA-4 switches off the activation of the T cell. The interaction between the B7 proteins with CD28 and/or CTLA-4 constitute a costimulatory signalling pathway which plays an important role in immune activation and regulation. Thus, the B7 molecules are part of a pathway, amenable to manipulation in order to uncouple immune inhibition, thereby enhancing immunity in patients.

The CD86 protein is a monomer and consists of two extracellular immunoglobulin superfamily domains. The receptor binding domain of CD86 has a typical IgV-set structure, whereas the membrane proximal domain has a C1-set like structure. The structures of CD80 and CD86 have been determined on their own or in complex with CTLA-4. The contact residues on the CD80 and CD86 molecules are in the soluble extracellular domain, and mostly located in the beta-sheets and not in the (CDR-like) loops. The amino acid sequence of the monomeric soluble extracellular domain of human wild-type CD86 is provided as SEQ ID NO: 3. This wild type sequence may optionally lack Alanine and Proline at the N terminus, that is positions 24 and 25. These amino acids may be referred to herein as A24 and P25 respectively.

The Polypeptides of the Invention

The present invention relates to poylpeptides that bind to CTLA-4 and may also bind to CD28. The term CTLA-4 as used herein typically refers to human CTLA-4 and the term CD28 as used herein typically refers to human CD28, but may refer to CTLA-4 or CD28 from other mammals, for example primate or murine CTLA-4 or CD28. The sequences of human CTLA-4 and human CD28 are set out in SEQ ID NOs: 1 and 2 respectively. The sequences of murine CTLA-4 and murine CD28 are set out in SEQ ID NOs: 45 and 46, respectively. A polypeptide of the present invention may have some binding affinity for CTLA-4 or CD28 from other mammals, for example primate or murine CTLA-4 or CD28.

A polypeptide of the invention has the ability to bind to CTLA-4 in its native state and in particular to CTLA-4 localised on the surface of a cell. By "localised on the surface of a cell" it is meant that CTLA-4 is associated with the cell such that one or more region of CTLA-4 is present on the outer face of the cell surface. For example, CTLA-4 may be inserted into the cell plasma membrane (i.e. orientated as a transmembrane protein) with one or more regions presented on the extracellular surface. This may occur in the course of expression of CTLA-4 by the cell. Thus, in one embodiment, "localised on the surface of a cell" may mean "expressed on the surface of a cell." Alternatively, CTLA-4 may be outside the cell with covalent and/or ionic interactions localising it to a specific region or regions of the cell surface.

A polypeptide of the invention has different properties compared to human wild-type CD86. Specifically, a polypeptide of the invention has different target binding properties compared to the target binding properties of human wild-type CD86. For the purposes of comparing such properties, "human wild-type CD86" typically refers to the monomeric soluble extracellular domain of human wild-type CD86 as described in the preceding section.

Human wild-type CD86 specifically binds to two targets, CTLA-4 and CD28. Accordingly, the binding properties of a polypeptide described herein may be expressed as an individual measure of the ability of the polypeptide to bind to each of these targets. For example, a polypeptide of the invention preferably binds to CTLA-4 with a higher binding affinity than that of wild-type human CD86 for CTLA-4. A polypeptide of the invention may optionally also bind to CD28 with a lower binding affinity than that of wild-type human CD86 for CD28.

Standard assays to evaluate the binding ability of ligands towards targets are well known in the art, including for example, ELISAs, Western blots, RIAs, and flow cytometry analysis. The binding kinetics (e.g., binding affinity) of the polypeptide also can be assessed by standard assays known in the art, such as by Surface Plasmon Resonance analysis (SPR).

The terms "binding activity" and "binding affinity" are intended to refer to the tendency of a polypeptide molecule to bind or not to bind to a target. Binding affinity may be quantified by determining the dissociation constant (Kd) for a polypeptide and its target. A lower Kd is indicative of a higher affinity for a target. Similarly, the specificity of binding of a polypeptide to its target may be defined in terms of the comparative dissociation constants (Kd) of the polypeptide for its target as compared to the dissociation constant with respect to the polypeptide and another, non-target molecule.

The value of the dissociation constant Kd can be determined directly by well-known methods, and can be computed even for complex mixtures by methods such as those, for example, set forth in Caceci et al. (Byte 9:340-362, 1984). For example, the Kd may be established using a double-filter nitrocellulose filter binding assay such as that disclosed by Wong & Lohman (Proc. Natl. Acad. Sci. USA 90, 5428-5432, 1993). A competitive binding assay can be conducted in which the binding of the polypeptide to the target is compared to the binding of the target by another, known ligand of that target, such as another polypeptide. In this case, the soluble extracellular domain of wild-type human CD86 (optionally linked to a detectable domain such as an Fc domain or an Ig domain at the N or C terminus) is a suitable alternative ligand. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

Alternative measures of binding affinity include EC50 or IC50. In this context EC50 indicates the concentration at which a polypeptide achieves 50% of its maximum binding to a fixed quantity of target. IC50 indicates the concentration at which a polypeptide inhibits 50% of the maximum binding of a fixed quantity of competitor to a fixed quantity of target. In both cases, a lower level of EC50 or IC50 indicates a higher affinity for a target. The EC50 and IC50 values of a ligand for its target can both be determined by well-known methods, for example ELISA. Suitable assays to assess the EC50 and IC50 of polypeptides of the invention are set out in the Examples.

The present invention relates to polypeptides that bind specifically bind to CTLA-4. That is, a polypeptide of the invention will preferably bind to CTLA-4 with greater binding affinity than that at which it binds to another molecule. The polypeptide preferably binds to CTLA-4 with with higher affinity than that of wild-type human CD86 for human CTLA-4.

Preferably, the Kd of the polypeptide for human CTLA-4 will be at least 2-fold, at least 2.5-fold, at least 3-fold, at least 3.5-fold, at least 4-fold, at least 4.5-fold, at least 5-fold, at least 5.5-fold, at least 8-fold or at least 10-fold less than the Kd of wild-type human CD86 for human CTLA-4. Most preferably, the Kd of the polypeptide for human CTLA-4 will be at least 5-fold or at least 10-fold less than the Kd of wild-type human CD86 for human CTLA-4. A preferred method for determining the Kd of a polypeptide of the invention for CTLA-4 is SPR analysis, e.g. with a Biacore™ system. Suitable protocols for the SPR analysis of polypeptides of the invention are set out in the Examples.

Preferably, the EC50 of the polypeptide of the invention for human CTLA-4 will be at least 1.5-fold, at least 2-fold, at least 3-fold, at least 5-fold, at least 10-fold, at least 12-fold, at least 14-fold, at least 15-fold, at least 17-fold, at least 20-fold, at least 25-fold or at least 50-fold less than the EC50 of wild-type human CD86 for human CTLA-4 under the same conditions. Most preferably, the EC50 of the polypeptide for human CTLA-4 will be at least 10-fold or at least 25-fold less than the EC50 of wild-type human CD86 for human CTLA-4 under the same conditions. A preferred method for determining the EC50 of a polypeptide of the invention for CTLA-4 is via ELISA. Suitable ELISA assays for use in the assessment of the EC50 of polypeptides of the invention are set out in the Examples.

Preferably, the IC50 of the polypeptide of the invention when competing with wild-type human CD86 for binding to human CTLA-4 will be at least 2-fold, at least 3-HI fold, at least 4-fold, at least 5-fold, at least 10-fold, at least 13-fold, at least 15-fold, at least 50-fold, at least 100-fold, or at least 300-fold less than the IC50 of wild-type human CD86 under the same conditions. Most preferably, the IC50 of the polypeptide will be at least 10-fold or at least 300-fold less than the IC50 of wild-type human CD86 under the same conditions. A preferred method for determining the IC50 of a polypeptide of the invention is via ELISA. Suitable ELISA assays for use in the assessment of the IC50 of polypeptides of the invention are set out in the Examples.

The polypeptide may also bind specifically to CD28. That is, a polypeptide of the invention may bind to CD28 with greater binding affinity than that at which it binds to another molecule, with the exception of CTLA-4. The polypeptide may bind to human CD28 with a lower affinity than that of wild-type human CD86 for human CD28. Preferably, the Kd of the polypeptide for human CD28 will be at least 2-fold, preferably at least 5-fold, more preferably at least 10-fold higher than the Kd of wild-type human CD86 for human CD28.

The binding properties of the polypeptides described herein may also be expressed as a relative measure of the ability of a polypeptide to bind to the two targets, CTLA-4 and CD28. That is, the binding properties of a polypeptide may be expressed as a relative measure of the ability of the polypeptide to bind to CTLA-4 versus its ability to bind to CD28. Preferably the polypeptide of the invention has an increased relative ability to bind to CTLA-4 versus CD28, when compared to the corresponding relative ability of human wild-type CD86 to bind to CTLA-4 versus CD28.

When the binding affinity of a polypeptide for both CTLA-4 and CD28 is assessed using the same parameter (e.g. Kd, EC50), then the relative binding ability of the polypeptide for each target may be expressed as a simple ratio of the values of the parameter for each target. This ratio may be referred to as the binding ratio or binding strength ratio of a polypeptide. For many parameters used to assess binding affinity (e.g. Kd, EC50), a lower value indicates a higher affinity. When this is the case, the ratio of binding affinities for CTLA-4 versus CD28 is preferably expressed as a single numerical value calculated according to the following formula:

Binding ratio=[binding affinity for CD28]÷[binding affinity for CTLA-4]

Alternatively, if binding affinity is assessed using a parameter for which a higher value indicates a higher affinity, the inverse of the above formula is preferred. In either context, a polypeptide of the invention preferably has a higher binding ratio than human wild-type CD86. It will be appreciated that direct comparison of the binding ratio for a given polypeptide to the binding ratio for another polypeptide typically requires that the same parameters be used to assess the binding affinities and calculate the binding ratios for both polypeptides.

Preferably, the binding ratio for a polypeptide is calculated by determining the Kd of the polypeptide for each target and then calculating the ratio in accordance with the formula [Kd for CD28]÷[Kd for CTLA-4]. This ratio may be referred to as the Kd binding ratio of a polypeptide. A preferred method for determining the Kd of a polypeptide for a target is SPR analysis, e.g. with a Biacore™ system. Suitable protocols for the SPR analysis of polypeptides of the invention are set out in the Examples. The binding ratio of a polypeptide of the invention calculated according to this method is preferably at least 2-fold or at least 4-fold higher than the binding ratio of wild-type human CD86 calculated according to the same method.

Alternatively, the binding ratio for a polypeptide may be calculated by determining the EC50 of the polypeptide for each target and then calculating the ratio in accordance with the formula [EC50 for CD28]÷[EC50 for CTLA-4]. This ratio may be referred to as the EC50 binding ratio of a polypeptide. A preferred method for determining the EC50 of a polypeptide for a target is via ELISA. Suitable ELISA assays for use in the assessment of the EC50 of polypeptides of the invention are set out in the Examples. The binding ratio of a polypeptide of the invention calculated according to this method is at least 2-fold, at least 3-fold, at least 4-fold, at least 5-fold, at least 6-fold, at least 7-fold, at least 8-fold, at least 9-fold or at least 10-fold higher than the binding ratio of wild-type human CD86 calculated according to the same method.

A polypeptide of the invention may have the ability to cross-compete with another polypeptide of the invention for binding to CTLA-4. For example, a polypeptide of the invention may cross-compete with a polypeptide comprising or consisting of the amino acid sequence of any one of SEQ ID NOs: 6 to 24 for binding to CTLA-4. Such cross-competing polypeptides may be identified in standard binding assays. For example, SPR analysis (e.g. with a BIACORE™ system), ELISA assays or flow cytometry may be used to demonstrate cross-competition. Such an assay may be used to identify other CTLA-4 binding polypeptides. The candidates in such an assay preferably do not comprise an amino acid sequence which is identical to SEQ ID NO: 3.

In addition to the above functional characteristics, a polypeptide of the invention has certain preferred structural characteristics. A polypeptide of the invention comprises an amino acid sequence derived from the amino acid sequence of human wild-type CD86, specifically the amino acid sequence of the soluble extracellular domain of human wild-type CD86 (SEQ ID NO: 3), optionally lacking A24 and P25. In particular, a polypeptide of the invention comprises an amino acid sequence in which at least one amino acid is changed when compared to the amino acid sequence of SEQ ID NO: 3 (or said sequence lacking A24 and P25). By "changed" it is meant that at least one amino acids is deleted, inserted, or substituted compared to the amino acid sequence of SEQ ID NO: 3 (or said sequence lacking A24 and P25). By "deleted" it is meant that the at least one amino acid present in the amino acid sequence of SEQ ID NO: 3 (or said sequence lacking A24 and P25) is removed, such that the amino acid sequence is shortened by one amino acid. By "inserted" it is meant that the at least one additional amino acid is introduced into the amino acid sequence of SEQ ID NO: 3 (or said sequence lacking A24 and P25), such that the amino acid sequence is lengthened by one amino acid. By "substituted" it is meant that the at least one amino acid in the amino acid sequence of SEQ ID NO: 3 (or said sequence lacking A24 and P25) is replaced with an alternative amino acid.

Amino acids herein may be referred to by full name, three letter code or single letter code, as set out below.

| | | |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Typtophan | Trp | W |
| Tyrosine | Tyr | Y |
| Valine | Val | V |

Typically, at least 1, 2, 3, 4, 5, 6, 7, 8 or 9 amino acids are changed when compared to the amino acid sequence of SEQ ID NO: 3 (or said sequence lacking A24 and P25). Typically, no more than 10, 9, 8, 7, 6, 5, 4, 2 or 1 amino acids are changed when compared to the amino acid sequence of SEQ ID NO: 3 (or said sequence lacking A24 and P25). It will be appreciated that any of these lower limits may be combined with any of these upper limits to define a range for the permitted number of changes compared to the amino acid sequence of SEQ ID NO: 3 (or said sequence lacking A24 and P25). Thus, for example, a polypeptide of the invention may comprise an amino acid sequence in which the permitted number of amino acid changes compared to the amino acid sequence of SEQ ID NO: 3 (or said sequence lacking A24 and P25) is in the range 2 to 3, 2 to 4, 2 to 5, 2 to 6, 2 to 7, 2 to 8, 2 to 9, 2 to 10, 3 to 4, 3 to 5, 3 to 6, and so on.

It is particularly preferred that at least 2 amino acids are changed when compared to the amino acid sequence of SEQ ID NO: 3 (or said sequence lacking A24 and P25). Preferably, the permitted number of amino acid changes compared to the amino acid sequence of SEQ ID NO: 3(or said sequence lacking A24 and P25) is in the range 2 to 9, 2 to 8 or 2 to 7.

The numbers and ranges set out above may be achieved with any combination of deletions, insertions or substitutions compared to the amino acid sequence of SEQ ID NO: 3(or said sequence lacking A24 and P25). For example, there may be only deletions, only insertions, or only substitutions compared to the amino acid sequence of SEQ ID NO: 3 (or said sequence lacking A24 and P25), or any mixture of deletions, insertions or substitutions. Preferably the polypeptide of the invention comprises an amino acid sequence in which all of the changes compared to the amino acid sequence of SEQ ID NO: 3 (or said sequence lacking A24 and P25) are substitutions. That is, a sequence in which no amino acids are deleted or inserted compared to the sequence of SEQ ID NO: 3 (or said sequence lacking A24 and P25). In the amino acid sequence of a preferred polypeptide of the invention, 1, 2, 3, 4, 5, 6, 7, or 8 amino acids are substituted when compared to the amino acid sequence of SEQ ID NO: 3 (or said sequence lacking A24 and P25) and no amino acids are deleted or inserted compared to the sequence of SEQ ID NO: 3 (or said sequence lacking A24 and P25).

Preferably the changes compared to the sequence of SEQ ID NO: 3 (or said sequence lacking A24 and P25) are in the FG loop region (positions 114 to 121) and/or the beta sheet region of SEQ ID NO: 3. The strands of the beta sheet region have the following positions in SEQ ID NO: 3: A:27-31, B:36-37, C:54-58, C':64-69, C":72-74, D:86-88, E:95-97, F:107-113, G:122-133.

Most preferably, the changes compared to the sequence of SEQ ID NO: 3 (or said sequence lacking A24 and P25) are in one or more of the positions selected from 32, 48, 49, 54, 74, 77, 79, 103, 107, 111, 118, 120, 121, 122, 125, 127 or 134. All numbering of amino acid positions herein is based on counting the amino acids in SEQ ID NO: 4 starting from the N terminus. Thus, the first position at the N terminus of SEQ ID NO: 3 is numbered 24 (see schematic diagram in FIG. 4).

Particularly preferred insertions include a single additional amino acid inserted between positions 116 and 117 and/or a single additional amino acid inserted between positions 118 and 119. The inserted amino acid is preferably Tyrosine (Y), Serine (S), Glycine (G), Leucine (L) or Aspartic Acid (D).

A particularly preferred substitution is at position 122, which is Arginine (R). The polypeptide of the invention preferably includes an amino acid sequence in which position 122 is substituted compared to the amino acid sequence of SEQ ID NO: 3 (or said sequence lacking A24 and P25). The most preferred substitution at position 122 is to replace Arginine (R) with Lysine (K) or Asparagine (N), ranked in order of preference. This substitution may be referred to as R122K/N.

Other preferred substitutions are at positions 107, 121, and 125, which are Leucine (L), Isoleucine (I) and Glutamic acid (Q), respectively. In addition to the substitution at position 122, the polypeptide of the invention preferably includes an amino acid sequence in which at least one of the amino acids at positions 107, 121 and 125 is also substituted compared to the amino acid sequence of SEQ ID NO: 3 (or said sequence lacking A24 and P25). The amino acid sequence of the polypeptide of the invention may also be substituted at one or more of positions 32, 48, 49, 54, 64, 74, 77, 79, 103, 111, 118, 120, 127 and 134.

The most preferred substitution at position 107 is to replace Leucine (L) with Isoleucine(I), Phenylalanine(F) or Arginine(R), ranked in order of preference. This substitution may be referred to as L107I/F/R. Similar notation is used for other substitutions described herein. The most preferred substitution at position 121 is to replace Isoleucine (I) with Valine (V). This substitution may be referred to as I121 V. The most preferred substitution at position 125 is to replace Glutamine (Q) with Glutamic acid (E). This substitution may be referred to as Q125E.

Other substitutions which may be preferred in the amino acid sequence of the polypeptide of the invention include: F32I, Q48L, S49T, V54I, V64I, K74I/R, S77A, H79D/S/A, K103E, I111V, T118S, M120L, N127S/D and A134T.

Particularly preferred polypeptides of the invention comprise or consist of any one of the following amino acid sequences of SEQ ID NOs: 6 to 24

| SEQ ID NO. | DESIGNATION | SEQUENCE |
|---|---|---|
| 6 | 900 | LKIQAYFNETADLPCQFANSQNQSLSELVVFWQDQENLVLNEVYLGKEKFDSVDSK<br>YMGRTSFDSDSWTLRLHNLQIKDKGIYQCVIHHKKPSGLVKIHEMNSELSVLA |
| 7 | 901 | LKIQAYFNETADLPCQFANSQNLTLSELVVFWQDQENLVLNEVYLGKEKFDSVHSK<br>YMGRTSFDSDSWTLRLHNLQIKDKGIYQCVIHHKKPTGMIKIHEMNSELSVLT |
| 8 | 904 | LKIQAYFNETADLPCQFANSQNQSLSELIVFWQDQENLVLNEVYLGKERFDAVDSK<br>YMGRTSFDSDSWTLRLHNLQIKDKGIYQCIIHHKKPSGMVKIHQMDSELSVLA |
| 9 | 906 | LKIQAYINETADLPCQFANSQNLSLSELVVFWQDQENLVLNEVYLGKERFDSVDSK<br>YMGRTSFDSDSWTLRLHNLQIKDKGFYQCIIHHKKPTGLVKIHEMNSELSVLA |
| 10 | 907 | LKIQAYFNETADLPCQFANSQNQSLSELVVFWQDQENLVLNEVYLGKEKFDSVHSK<br>YMGRTSFDSDSWTLRLHNLQIKDKGLYQCIIHHKKPTGMIKIHEMNSELSVLA |
| 11 | 908 | LKIQAYFNETADLPCQFANSQNQSLSELVVFWQDQENLVLNEVYLGKEKFDSVHSK<br>YMGRTSFDSDSWTLRLHNLQIKDKGIYQCIIHHKKPTGMVKIHEMNSELSVLA |
| 12 | 910 | LKIQAYFNETADLPCQFANSQNQSLSELVVFWQDQENLVLNEVYLGKEKFDSVDSK<br>YMGRTSFDSDSWTLRLHNLQIKDKGIYQCIIHHKKPTGMVKIHEMNSELSVLA |
| 13 | 915 | LKIQAYFNETADLPCQFANSQNQSLSELVVFWQDQENLILNEVYLGKEKFDSVDSK<br>YMGRTSFDSDSWTLRLHNLQIKDKGFYQCIIHHKKPSGLIKIHQMDSELSVLA |

| SEQ ID NO. | DESIGNATION | SEQUENCE |
|---|---|---|
| 14 | 938 | LKIQAYFNETADLPCQFANSQNQSLSELVVFWQDQENLILNEVYLGKEKFDSVHSK YMGRTSFDSDSWTLRLHNLQIKDKGIYQCIIHHKKPTGMVKIHQMNSELSVLA |
| 15 | 1038 | APLKIQAYFNETADLPCQFANSQNLSLSELVVFWQDQENLVLNEVYLGKEKFDSVD SKYMGRTSFDSDSWTLRLHNLQIKDKGIYQCIIHHKKPTGMVKIHEMNSELSVLA |
| 16 | 1039 | APLKIQAYFNETADLPCQFANSQNLSLSELVVFWQDQENLVLNEVYLGKEKFDSVS SKYMGRTSFDSDSWTLRLHNLQIKDKGIYQCIIHHKKPSGMVKIHQMDSELSVLA |
| 17 | 1040 | APLKIQAYFNETADLPCQFANSQNLSLSELVVFWQDQENLVLNEVYLGKERFDSVD SKYMGRTSFDSDSWTLRLHNLQIKDKGRYQCIIHHKKPTGMINIHQMNSELSVLA |
| 18 | 1041 | APLKIQAYLNETADLPCQFANSQNLSLSELVVFWQDQENLVLNEVYLGKEKFDSVD SKYMGRTSFDSDSWTLRLHNLQIKDKGIYQCIIHHKKPTGLVKIHEMNSELSVLA |
| 19 | 1042 | APLKIQAYFNETADLPCQFANSQNLSLSELVVFWQDQENLVLNEVYLGKEIFDSVS SKYMGRTSFDSDSWTLRLHNLQIKDKGIYQCIIHHKKPSGMVKIHQMDSELSVLA |
| 20 | 1043 | APLKIQAYFNETADLPCQFANSQNLSLSELVVFWQDQENLVLNEVYLGKEKFDSVD SKYMGRTSFDSDSWTLRLHNLQIKDKGIYQCIIHHKKPTGMIKIHEMNSELSVLA |
| 21 | 1044 | APLKIQAYFNETADLPCQFANSQNLTLSELVVFWQDQENLVLNEVYLGKEKFDSVS SKYMGRTSFDSDSWTLRLHNLQIKDKGIYQCIIHHKKPTGMIKIHEMSSELSVLA |
| 22 | 1045 | APLKIQAYFNETADLPCQFANSQNLTLSELVVFWQDQENLVLNEVYLGKEKFDSVD SKYMGRTSFDSDSWTLRLHNLQIKDKGLYQCIIHHKKPTGLVKIHEMNSELSVLA |
| 23 | 1046 | APLKIQAYFNETADLPCQFANSQNQSLSELVVFWQDQENLVLNEVYLGKEKFDSVD SKYMGRTSFDSDSWTLRLHNLQIEDKGIYQCIIHHKKPSGMVKIHQMDSELSVLA |
| 24 | 1047 | APLKIQAYFNETADLPCQFANSQNLSLSELVVFWQDQENLVLNEVYLGKEKFDSVD SKYMGRTSFDSDSWTLRLHNLQIKDKGIYQCIIHHKKPTGLVKIHEMNSELSVLA |

The amino acid sequences shown in SEQ ID NOs: 6 to 14 may optionally include the additional residues AP at the N-terminus. The amino acid sequences shown in SEQ ID NOs: 15 to 24 may optionally lack the residues AP at the N-terminus. In either case, these residues correspond to A24 and P25 of SEQ ID NO: 3.

A polypeptide of the invention may be prepared by any suitable means. For example, the polypeptide may be expressed by a cell comprising a nucleotide which encodes said polypeptide as is explained in more detail below. Alternatively the polypeptide may be synthesised de novo by any suitable method.

A polypeptide of the invention may be provided in isolated or substantially isolated form. By substantially isolated, it is meant that there may be substantial, but not total, isolation of the polypeptide from any surrounding medium. The polypeptides may be mixed with carriers or diluents which will not interfere with their intended use and still be regarded as substantially isolated.

A polypeptide of the invention may be attached (directly or indirectly) to another molecule. The other molecule may be a polypeptide such as an Fc domain or an Ig domain attached to the N or C terminus of the polypeptide of the invention. The polypeptide of the invention may be attached to albumin or albumin binding modules, or, alternatively be attached to PEG. In particular embodiments, the other molecule may be a therapeutic agent or a detectable label. Suitable therapeutic agents include a cytotoxic moiety or a drug.

The other molecule may be directly attached, for example by chemical conjugation, to a polypeptide of the invention. Where the other molecule is a polypeptide, the polypeptide of the invention and the other polypeptide may be linked by a peptide bond, for example as a fusion protein. Other methods for conjugating molecules to polypeptides are known in the art. For example, carbodiimide conjugation (Bauminger & Wilchek (1980) Methods Enzymol. 70, 151-159) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety. As a further example, conjugation may be achieved by sodium periodate oxidation followed by reductive alkylation of appropriate reactants, or by glutaraldehyde cross-linking. However, it is recognised that, regardless of which method is selected, a determination must be made that the polypeptide of the invention retains its target binding properties.

Functional Effects of Binding to CTLA-4

A polypeptide of the invention may modulate signalling from CTLA-4, for example when administered to a cell expressing CTLA-4, such as a T cell. Preferably the polypeptide reduces, i.e. inhibits or blocks, said signalling and thereby increases the activation of said cell. Changes in CTLA-4 signalling and cell activation as a result of administration of a test agent (such as a polypeptide of the invention) may be determined by any suitable method. Suitable methods include assaying for the ability of membrane-bound CD86 (e.g. on Raji cells) to bind and signal through CTLA-4 expressed on the surface of T cells, when in the presence of a test agent or in the presence of a suitable control. An increased level of T cell IL-2 production or an increase in T cell proliferation in the presence of the test agent relative to the level of T cell IL-2 production and/or T cell proliferation in the presence of the control is indicative of reduced signalling through CTLA-4 and increased cell activation. A typical assay of this type is disclosed in Example 9 of US20080233122.

Polynucleotides, Vectors and Cells

The invention also relates to polynucleotides that encode polypeptides of the invention. Thus, a polynucleotide of the invention may encode any polypeptide as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises any one of SEQ ID NOS: 25 to 43 as set out below.

```
25    900    CTCAAAATCCAAGCGTACTTCAACGAAACTGCAGACTTACCGTGTCAGTTTGCCAA
             TTCGCAGAATCAAAGCCTGAGCGAACTGGTGGTTTTCTGGCAGGATCAGGAGAACC
             TGGTTCTGAACGAAGTCTATCTGGGCAAAGAGAAATTCGACAGCGTGGACAGCAAG
             TATATGGGCCGCACCAGCTTTGATAGCGACAGCTGGACCCTGCGTCTGCACAATCT
             GCAAATCAAAGATAAGGGTATCTACCAGTGCGTGATCCACCATAAGAAGCCGAGCG
             GTCTGGTGAAGATTCACGAGATGAACTCCGAGTTGTCTGTCCTGGCG 26    901    CTCAAAATCCAAGCGTACTTCAACGAAACTGCAGACTTACCGTGTCAGTTTGCCAA
             TTCGCAGAATCTGACCCTGAGCGAACTGGTGGTTTTCTGGCAGGATCAGGAGAACC
             TGGTTCTGAACGAAGTCTATCTGGGCAAAGAGAAATTCGACAGCGTGCATAGCAAG
             TATATGGGCCGCACCAGCTTTGATAGCGACAGCTGGACCCTGCGTCTGCACAATCT
             GCAAATCAAAGATAAGGGTATCTACCAGTGCGTGATCCACCATAAGAAGCCGACGG
             GTATGATTAAGATTCACGAGATGAACTCCGAGTTGTCTGTCCTGACC 27    904    CTCAAAATCCAAGCGTACTTCAACGAAACTGCAGACTTACCGTGTCAGTTTGCCAA
             TTCGCAGAATCAAAGCCTGAGCGAACTGATCGTTTTCTGGCAGGATCAGGAGAACC
             TGGTTCTGAACGAAGTCTATCTGGGCAAAGAGCGGTTCGACGCCGTGGACAGCAAG
             TATATGGGCCGCACCAGCTTTGATAGCGACAGCTGGACCCTGCGTCTGCACAATCT
             GCAAATCAAAGATAAGGGTATCTACCAGTGCATTATCCACCATAAGAAGCCGAGCG
             GTATGGTGAAGATTCACCAAATGGACTCCGAGTTGTCTGTCCTGGCG 28    906    CTCAAAATCCAAGCGTACATCAACGAAACTGCAGACTTACCGTGTCAGTTTGCCAA
             TTCGCAGAATCTGAGCCTGAGCGAACTGGTGGTTTTCTGGCAGGATCAGGAGAACC
             TGGTTCTGAACGAAGTCTATCTGGGCAAAGAGCGGTTCGACAGCGTGGACAGCAAG
             TATATGGGCCGCACCAGCTTTGATAGCGACAGCTGGACCCTGCGTCTGCACAATCT
             GCAAATCAAAGATAAGGGTTCTACCAGTGCATTATCCACCATAAGAAGCCGACGG
             GTCTGGTGAAGATTCACGAGATGAACTCCGAGTTGTCTGTCCTGGCG 29    907    CTCAAAATCCAAGCGTACTTCAACGAAACTGCAGACTTACCGTGTCAGTTTGCCAA
             TTCGCAGAATCAAAGCCTGAGCGAACTGGTGGTTTTCTGGCAGGATCAGGAGAACC
             TGGTTCTGAACGAAGTCTATCTGGGCAAAGAGAAATTCGACAGCGTGCATAGCAAG
             TATATGGGCCGCACCAGCTTTGATAGCGACAGCTGGACCCTGCGTCTGCACAATCT
             GCAAATCAAAGATAAGGGTCTGTACCAGTGCATTATCCACCATAAGAAGCCGACGG
             GTATGATTAAGATTCACGAGATGAACTCCGAGTTGTCTGTCCTGGCG 30    908    CTCAAAATCCAAGCGTACTTCAACGAAACTGCAGACTTACCGTGTCAGTTTGCCAA
             TTCGCAGAATCAAAGCCTGAGCGAACTGGTGGTTTTCTGGCAGGATCAGGAGAACC
             TGGTTCTGAACGAAGTCTATCTGGGCAAAGAGAAATTCGACAGCGTGCATAGCAAG
             TATATGGGCCGCACCAGCTTTGATAGCGACAGCTGGACCCTGCGTCTGCACAATCT
             GCAAATCAAAGATAAGGGTATCTACCAGTGCATTATCCACCATAAGAAGCCGACGG
             GTATGGTGAAGATTCACGAGATGAACTCCGAGTTGTCTGTCCTGGCG 31    910    CTCAAAATCCAAGCGTACTTCAACGAAACTGCAGACTTACCGTGTCAGTTTGCCAA
             TTCGCAGAATCAAAGCCTGAGCGAACTGGTGGTTTTCTGGCAGGATCAGGAGAACC
             TGGTTCTGAACGAAGTCTATCTGGGCAAAGAGAAATTCGACAGCGTGGACAGCAAG
             TATATGGGCCGCACCAGCTTTGATAGCGACAGCTGGACCCTGCGTCTGCACAATCT
             GCAAATCAAAGATAAGGGTATCTACCAGTGCATTATCCACCATAAGAAGCCGACGG
             GTATGGTGAAGATTCACGAGATGAACTCCGAGTTGTCTGTCCTGGCG 32    915    CTCAAAATCCAAGCGTACTTCAACGAAACTGCAGACTTACCGTGTCAGTTTGCCAA
             TTCGCAGAATCAAAGCCTGAGCGAACTGGTGGTTTTCTGGCAGGATCAGGAGAACC
             TGATCCTGAACGAAGTCTATCTGGGCAAAGAGAAATTCGACAGCGTGGACAGCAAG
             TATATGGGCCGCACCAGCTTTGATAGCGACAGCTGGACCCTGCGTCTGCACAATCT
             GCAAATCAAAGATAAGGGTTCTACCAGTGCATTATCCACCATAAGAAGCCGAGCG
             GTCTGATTAAGATTCACCAAATGGACTCCGAGTTGTCTGTCCTGGCG
```

-continued

| | | |
|---|---|---|
| 33 | 938 | CTCAAAATCCAAGCGTACTTCAACGAAACTGCAGACTTACCGTGTCAGTTTGCCAA<br>TTCGCAGAATCTGAGCCTGAGCGAACTGGTGGTTTTCTGGCAGGATCAGGAGAACC<br>TGATCCTGAACGAAGTCTATCTGGGCAAAGAGCGGTTCGACAGCGTGCATAGCAAG<br>TATATGGGCCGCACCAGCTTTGATAGCGACAGCTGGACCCTGCGTCTGCACAATCT<br>GCAAATCAAAGATAAGGGTCTGTACCAGTGCATTATCCACCATAAGAAGCCGAGCG<br>GTATGGTGAAGATTCACGAGATGAACTCCGAGTTGTCTGTCCTGGCG |
| 34 | 1038 | GCCCCCCTCAAAATCCAAGCGTACTTCAACGAAACTGCAGACTTACCGTGTCAGTT<br>TGCCAATTCGCAGAATCTGAGCCTGAGCGAACTGGTGGTTTTCTGGCAGGATCAGG<br>AGAACCTGGTTCTGAACGAAGTCTATCTGGGCAAAGAGAAATTCGACAGCGTGGAC<br>AGCAAGTATATGGGCCGCACCAGCTTTGATAGCGACAGCTGGACCCTGCGTCTGCA<br>CAATCTGCAAATCAAAGATAAGGGTATCTACCAGTGCATTATCCACCATAAGAAGC<br>CGACGGGTATGGTGAAGATTCACGAGATGAACTCCGAGTTGTCTGTCCTGGCG |
| 35 | 1039 | GCCCCCCTCAAAATCCAAGCGTACTTCAACGAAACTGCAGACTTACCGTGTCAGTT<br>TGCCAATTCGCAGAATCTGAGCCTGAGCGAACTGGTGGTTTTCTGGCAGGATCAGG<br>AGAACCTGGTTCTGAACGAAGTCTATCTGGGCAAAGAGAAATTCGACAGCGTGAGT<br>AGCAAGTATATGGGCCGCACCAGCTTTGATAGCGACAGCTGGACCCTGCGTCTGCA<br>CAATCTGCAAATCAAAGATAAGGGTATCTACCAGTGCATTATCCACCATAAGAAGC<br>CGAGCGGTATGGTGAAGATTCACCAAATGGACTCCGAGTTGTCTGTCCTGGCG |
| 36 | 1040 | GCCCCCCTCAAAATCCAAGCGTACTTCAACGAAACTGCAGACTTACCGTGTCAGTT<br>TGCCAATTCGCAGAATCTGAGCCTGAGCGAACTGGTGGTTTTCTGGCAGGATCAGG<br>AGAACCTGGTTCTGAACGAAGTCTATCTGGGCAAAGAGCGGTTCGACAGCGTGGAC<br>AGCAAGTATATGGGCCGCACCAGCTTTGATAGCGACAGCTGGACCCTGCGTCTGCA<br>CAATCTGCAAATCAAAGATAAGGGTAGGTACCAGTGCATTATCCACCATAAGAAGC<br>CGACGGGTATGATTAATATTCACCAAATGAACTCCGAGTTGTCTGTCCTGGCG |
| 37 | 1041 | GCCCCCCTCAAAATCCAAGCGTACCTCAACGAAACTGCAGACTTACCGTGTCAGTT<br>TGCCAATTCGCAGAATCTGAGCCTGAGCGAACTGGTGGTTTTCTGGCAGGATCAGG<br>AGAACCTGGTTCTGAACGAAGTCTATCTGGGCAAAGAGAAATTCGACAGCGTGGAC<br>AGCAAGTATATGGGCCGCACCAGCTTTGATAGCGACAGCTGGACCCTGCGTCTGCA<br>CAATCTGCAAATCAAAGATAAGGGTATCTACCAGTGCATTATCCACCATAAGAAGC<br>CGACGGGTCTGGTGAAGATTCACGAGATGAACTCCGAGTTGTCTGTCCTGGCG |
| 38 | 1042 | GCCCCCCTCAAAATCCAAGCGTACTTCAACGAAACTGCAGACTTACCGTGTCAGTT<br>TGCCAATTCGCAGAATCTGAGCCTGAGCGAACTGGTGGTTTTCTGGCAGGATCAGG<br>AGAACCTGGTTCTGAACGAAGTCTATCTGGGCAAAGAGATTTTCGACAGCGTGAGT<br>AGCAAGTATATGGGCCGCACCAGCTTTGATAGTGACAGCTGGACCCTGCGTCTGCA<br>CAATCTGCAAATCAAAGATAAGGGTATCTACCAGTGCATTATCCACCATAAGAAGC<br>CGAGCGGTATGGTGAAGATTCACCAAATGGACTCCGAGTTGTCTGTCCTGGCG |
| 39 | 1043 | GCCCCCCTCAAAATCCAAGCGTACTTCAACGAAACTGCAGACTTACCGTGTCAGTT<br>TGCCAATTCGCAGAATCTGAGCCTGAGCGAACTGGTGGTTTTCTGGCAGGATCAGG<br>AGAACCTGGTTCTGAACGAAGTCTATCTGGGCAAAGAGAAATTCGACAGCGTGGAT<br>AGCAAGTATATGGGCCGCACCAGCTTTGATAGCGACAGCTGGACCCTGCGTCTGCA<br>CAATCTGCAAATCAAAGATAAGGGTATCTACCAGTGCATTATCCACCATAAGAAGC<br>CGACGGGTATGATTAAGATTCACGAGATGAACTCCGAGTTGTCTGTCCTGGCG |
| 40 | 1044 | GCCCCCCTCAAAATCCAAGCGTACTTCAACGAAACTGCAGACTTACCGTGTCAGTT<br>TGCCAATTCGCAGAATCTGACCCTGAGCGAACTGGTGGTTTTCTGGCAGGATCAGG<br>AGAACCTGGTTCTGAACGAAGTCTATCTGGGCAAAGAGAAATTCGACAGCGTGTCT<br>AGCAAGTATATGGGCCGCACCAGCTTTGATAGCGACAGCTGGACCCTGCGTCTGCA<br>CAATCTGCAAATCAAAGATAAGGGTATCTACCAGTGCATTATCCACCATAAGAAGC<br>CGACGGGTATGATTAAGATTCACGAGATGAGCTCCGAGTTGTCTGTCCTGGCG |
| 41 | 1045 | GCCCCCCTCAAAATCCAAGCGTACTTCAACGAAACTGCAGACTTACCGTGTCAGTT<br>TGCCAATTCGCAGAATCTGACCCTGAGCGAACTGGTGGTTTTCTGGCAGGATCAGG<br>AGAACCTGGTTCTGAACGAAGTCTATCTGGGCAAAGAGAAATTCGACAGCGTGGAC<br>AGCAAGTATATGGGCCGCACCAGCTTTGATAGCGACAGCTGGACCCTGCGTCTGCA<br>CAATCTGCAAATCAAAGATAAGGGTCTGTACCAGTGCATTATCCACCATAAGAAGC<br>CGACGGGTCTGGTGAAGATTCACGAGATGAACTCCGAGTTGTCTGTCCTGGCG |
| 42 | 1046 | GCCCCCCTCAAAATCCAAGCGTACTTCAACGAAACTGCAGACTTACCGTGTCAGTT<br>TGCCAATTCGCAGAATCAAAGCCTGAGCGAACTGGTGGTTTTCTGGCAGGATCAGG<br>AGAACCTGGTTCTGAACGAAGTCTATCTGGGCAAAGAGAAATTCGACAGCGTGGAC<br>AGCAAGTATATGGGCCGCACCAGCTTTGATAGCGACAGCTGGACCCTGCGTCTGCA<br>CAATCTGCAAATCGAAGATAAGGGTATCTACCAGTGCATTATCCACCATAAGAAGC<br>CGAGCGGTATGGTGAAGATTCACCAAATGGACTCCGAGTTGTCTGTCCTGGCG |
| 43 | 1047 | GCCCCCCTCAAAATCCAAGCGTACTTCAACGAAACTGCAGACTTACCGTGTCAGTT<br>TGCCAATTCGCAGAATCTGAGCCTGAGCGAACTGGTGGTTTTCTGGCAGGATCAGG<br>AGAACCTGGTTCTGAACGAAGTCTATCTGGGCAAAGAGAAATTCGACAGCGTGGAC<br>AGCAAGTATATGGGCCGCACCAGCTTTGATAGCGACAGCTGGACCCTGCGTCTGCA<br>CAATCTGCAAATCAAAGATAAGGGTATCTACCAGTGCATTATCCACCATAAGAAGC<br>CGACGGGTCTGGTGAAGATTCACGAGATGAACTCCGAGTTGTCTGTCCTGGCG |

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the University of Wisconsin Genetics Computer Group (UWGCG) Package provides the BESTFIT program which can be used to calculate homology (e.g. used on its default settings) (Devereux et al (1984) Nucleic Acids Research 12, p387-395).

The PILEUP and BLAST® algorithms can also be used to calculate homology or line up sequences (typically on their default settings), for example as described in Altschul S.F. (1993) J Mol Evol 36:290-300; Altschul, S, F et al (1990) J Mol Biol 215:403-10.

Software for performing BLAST® analysis is publicly available through the National Centre for Biotechnology Information (www.ncbi.nlm.nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST® algorithm parameters W, T and X determine the sensitivity and speed of the alignment. The BLAST® program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST® algorithm performs a statistical analysis of the similarity between two sequences; see e.g., Karlin and Altschul (1993) Proc. Natl. Acad. Sci. USA 90:5873-5787. One measure of similarity provided by the BLAST® algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

A polypeptide of the invention may thus be produced from or delivered in the form of a polynucleotide which encodes, and is capable of expressing, it.

Polynucleotides of the invention can be synthesised according to methods well known in the art, as described by way of example in Sambrook et at (1989, Molecular Cloning—a laboratory manual; Cold Spring Harbor Press).

The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art.

The invention also includes cells that have been modified to express a polypeptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an polypeptide of the invention include mammalian HEK293T, CHO, HeLa, NSO and COS cells. Preferably the cell line selected will be one which is not only stable, but also allows for mature glycosylation and cell surface expression of a polypeptide.

Such cell lines of the invention may be cultured using routine methods to produce an polypeptide of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

Pharmaceutical Formulations, Therapeutic and Other Uses and Patient Groups

In another aspect, the present invention provides compositions comprising molecules of the invention, such as the polypeptides, polynucleotides, vectors and cells described herein. For example, the invention provides a composition comprising one or more molecules of the invention, such as one or more polypeptides of the invention, and at least one pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the polypeptide may be coated in a material to protect the polypeptide from the action of acids and other natural conditions that may inactivate or denature the polypeptide.

Preferred pharmaceutically acceptable carriers comprise aqueous carriers or diluents. Examples of suitable aqueous carriers that may be employed in the compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. polypeptide) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Particularly preferred compositions are formulated for systemic administration or for local administration. Local administration may be at the site of a tumour or into a tumour draining lymph node. The composition may preferably be formulated for sustained release over a period of time. Thus the composition may be provided in or as part of a matrix facilitating sustained release. Preferred sustained release matrices may comprise a Montanide or γ-Polyglutamic acid (PGA) nanoparticles. Localised release of a polypeptide of the invention, optionally over a sustained period of time, may reduce potential autoimmune side-effects associated with administration of a CTLA-4 antagonist.

Compositions of the invention may comprise additional active ingredients as well as an polypeptide of the invention. As mentioned above, compositions of the invention may comprise one or more polypeptides of the invention. They may also comprise additional therapeutic or prophylactic agents.

Also within the scope of the present invention are kits comprising polypeptides or other compositions of the invention and instructions for use. The kit may further contain one ore more additional reagents, such as an additional therapeutic or prophylactic agent as discussed above.

The polypeptides in accordance with the present invention maybe used in therapy or prophylaxis. In therapeutic applications, polypeptides or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". In prophylactic applications, polypeptides or compositions are administered to a subject not yet exhibiting symptoms of a disorder or condition, in an amount sufficient to prevent or delay the development of symptoms. Such an amount is defined as a "prophylactically effective amount". The subject may have been identified as being at risk of developing the disease or condition by any suitable means.

Effective amounts for a given purpose will depend on the nature and severity of the disorder or condition, as well as the weight and general state of the subject. As used herein, the term "subject" includes any human.

In particular, polypeptides of the invention may be useful in the treatment or prevention of cancer. Accordingly, the invention provides a polypeptide of the invention for use in the treatment or prevention of cancer. The invention also provides a method of treating or preventing cancer comprising administering to an individual a polypeptide of the invention. The invention also provides an polypeptide of the invention for use in the manufacture of a medicament for the treatment or prevention of cancer.

The cancer may be prostate cancer, breast cancer, colorectal cancer, pancreatic cancer, ovarian cancer, lung cancer, cervical cancel, rhabdomyosarcoma, neuroblastoma, multiple myeloma, leukemia, acute lymphoblastic leukemia, melanoma, bladder cancer, gastric cancer, head and neck cancer, liver cancer, skin cancer, lymphoma or glioblastoma.

A polypeptide of the present invention, or a composition comprising said polypeptide, may be administered via one or more routes of administration using one or more of a variety of methods known in the art. As will be appreciated by the skilled artisan, the route and/or mode of administration will vary depending upon the desired results. Systemic administration or local administration are preferred. Local administration may be at the site of a tumour or into a tumour draining lymph node. Preferred modes of administration for polypeptides or compositions of the invention include intravenous, intramuscular, intradermal, intraperitoneal, subcutaneous, spinal or other parenteral modes of administration, for example by injection or infusion. The phrase "parenteral administration" as used herein means modes of administration other than enteral and topical administration, usually by injection. Alternatively, a polypeptide or composition of the invention can be administered via a non-parenteral mode, such as a topical, epidermal or mucosal mode of administration.

A suitable dosage of an polypeptide of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular polypeptide employed, the route of administration, the time of administration, the rate of excretion of the polypeptide, the duration of the treatment, other drugs, compounds and/or materials used in combination with the particular compositions employed, the age, sex, weight, condition, general health and prior medical history of the patient being treated, and like factors well known in the medical arts.

A suitable dose of an polypeptide of the invention may be, for example, in the range of from about 0.1 µg/kg to about 100 mg/kg body weight of the patient to be treated. For example, a suitable dosage may be from about 1 µg/kg to about 10 mg/kg body weight per day or from about 10 g/kg to about 5 mg/kg body weight per day.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Polypeptides may be administered in a single dose or in multiple doses. The multiple doses may be administered via the same or different routes and to the same or different locations. Alternatively, polypeptides can be administered as a sustained release formulation as described above, in which case less frequent administration is required. Dosage and frequency may vary depending on the half-life of the polypeptide in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Combined administration of two or more agents may be achieved in a number of different ways. In one embodiment, the polypeptide and the other agent may be administered together in a single composition. In another embodiment, the polypeptide and the other agent may be administered in separate compositions as part of a combined therapy. For example, the modulator may be administered before, after or concurrently with the other agent.

A polypeptide or composition of the invention may also be used in a method of increasing the activation of a cell expressing human CTLA-4, the method comprising administering to said cell a polypeptide or composition of the invention under conditions suitable to permit interaction between said cell and a polypeptide of the invention. The cell is typically a T cell. The method is typically carried out ex vivo.

The present invention is further illustrated by the following examples which should not be construed as further limiting. The contents of all figures and all references, patents and published patent applications cited throughout this application are expressly incorporated herein by reference.

EXAMPLES

Example 1

First Selection

Introduction

The starting material for the production of the polypeptides of the invention was the monomeric soluble extracellular binding domain of human CD86. That is, the CTLA-4 binding domain of human CD86. The amino acid sequence of this domain and a structural model of CD86 in complex with CTLA-4 (Schwartz et al; Nature 2001; 410(6828) p 604-608) was used to design 4 different starting phage display libraries of candidate polypeptides: AL-1014-01, AL-1014-02, AL-1014-03 and AL-1014-04. The phage display libraries were produced using standard protocols using nucleotide sequences encoding the candidate polypeptides. The amino acid sequences of the candidate polypeptides were designed as set out below.

Library Design

The primary purpose for the design of library AL-1014-01 was to provide an increased binding surface of the binding domain of CD86 for the interaction with CTLA-4. To this end, various residues in the FG loop of CD86 (positions 114 to 121, numbering as in FIG. 4) were selected for mutation. Two insertions were also introduced to allow for a elongation of the FG-loop. The positions and introduced mutations relative to the wild-type sequence of CD86 are summarised in Table 1 below. The variability that was allowed in each position is displayed. Nucleotides encoding all of the possible polypeptides which result from all of the possible combinations of the mutations shown in Table 1 were designed and used to produce the AL-1014-01 phage display library, in accordance with standard protocols.

TABLE 1

Amino acid sequence number according to SEQ ID NO: 1

| 113 | 114 | 115 | 116 | insert | 117 | 118 | insert | 119 | 120 | 121 | 122 | |
|---|---|---|---|---|---|---|---|---|---|---|---|---|
| H | H | K | K |   | P | T |   | G | M | I | R | Wt-sequence |
| Y | Y | Y | Y | Y | Y | Y | Y | Y | Y | Y | Y | Amino acids |
| S | S | S | S | S | S | S | S | S | S | S | S | allowed in each |
| G | G | G | G | G | G | G | G |   | G | G | G | position |
| L | L | L | L | L | L | L | L | L | L | L | L | (restricted) |
| D | D | D | D | D | D | D | D | D | D | D | D | variability) |
|   | K |   |   |   | R | K |   |   |   | K |   | |

In library AL-1014-02 amino acid positions in the binding surfaces of CD86 facing CTLA-4 were allowed to vary between the wild type amino acid and a very limited number of homologous residues to introduce minimal structural perturbations in the beta-sheet surface of CD86. The positions and introduced mutations of the library AL-1014-02 are shown in Table 2. A mutation in position 79 has been reported to contribute favorably to the binding of CD86 to CTLA-4 (Peach et al; Journal of Biological Chemistry 1995; 270 p 21181-21187), and this position was also allowed to vary in the library. The variability that was allowed in each position is displayed. Nucleotides encoding all of the possible polypeptides which result from all of the possible combinations of the mutations shown in Table 2 were designed and used to produce the AL-1014-02 phage display library, in accordance with standard protocols. Table 2 also shows the IUPAC-IUB code that was used to represent the indicated mutations in the corresponding nucleotide sequences. IUPAC-IUB codes are typically used to define multiple nucleotide possibilities in a given position and are based on a recognised set of nomeclature rules for incompletely specified bases in nucleotide sequences (see Biochem. J., 1985, 229, 281-286; Eur. J. Biochem., 1985, 150, 1-5; J. Biol. Chem., 1986, 261, 13-17; Mol. Biol. Evol., 1986, 3, 99-108; Nucl. Acids Res., 1985, 13, 3021-3030; Proc. Nat. Acad. Sci. (U. S.), 1986, 83, 4-8; and Biochemical Nomenclature and Related Documents 2nd edition, Portland Press, 1992, pp 122-126). The IUPAC-IUB codes used in these experiments are summarised below Table 2.

TABLE 2

| Amino acid sequence position in human CD86 - numbering as in FIG. 4 | | | | | | | | | | | |
|---|---|---|---|---|---|---|---|---|---|---|---|
| saa | rtt | Twc | Saa | rtt | gam | Twc | arg | kct | san | htc | Saa |
| 48 | 54 | 56 | 58 | 64 | 67 | 69 | 74 | 77 | 79 | 107 | 109 |
| Q | V | F | Q | V | E | Y | K | S | H | L | Q |
| E | I | Y | E | I | D | F | R | A | D | I | E |
| | | | | | | | | | E | F | |
| | | | | | | | | | Q | | |
| | | | | | | | | | A | | |

| Amino acid sequence position in human CD86 - numbering as in FIG. 4 | | | | | | | | | |
|---|---|---|---|---|---|---|---|---|---|
| Vtc | san | asc | gst | mtg | rtt | arg | saa | rac | IUB code |
| 111 | 113 | 118 | 119 | 120 | 121 | 122 | 125 | 127 | a.a. position |
| I | H | T | G | M | I | R | Q | N | Wt-sequ |
| L | D | S | A | L | V | K | E | D | Amino acids |
| V | E | | | | | | | | allowed in each |
| | Q | | | | | | | | position |
| | A | | | | | | | | (restricted variability) |

| IUPAC-IUB codes | | | | | | | | | | | |
|---|---|---|---|---|---|---|---|---|---|---|---|
| IUB Code | N | V | B | H | D | K | S | W | M | Y | R |
| Nucleotide bases | A, C, G, T | G, A, C | G, T, C | A, T, C | G, A, T | G, T | G, C | A, T | A, C | C, T | A, G |

Two more libraries were designed. In these two libraries, the entire IgGV domain of CD86 was randomized by taking the nucleotide sequence encoding wild type CD86 and using an error prone PCR method set-up to minimize mutational bias. The resulting mutant nucleotide sequences were used to produce phage display libraries in accordance with standard protocols.

Three different random mutagenized libraries were generated of which two were selected. AL-1014-03 was taken from randomization round 2 and randomization round 3 provided library AL-1014-04.

AL-1014-1, AL-1014-2, AL-1014-3 and AL-1014-04 were produced by cloning into a phagemid vector and phage stocks were generated according to standard protocols.

Selection Strategy

The selection strategy applied in this Example consisted of 6 rounds (R1 to R6) which are summarised in Table 3.

TABLE 3

| Selection round | Ag conc | Incubation (min) | Wash (min) | Non bio-Ag | Temp | pH | CD28 |
|---|---|---|---|---|---|---|---|
| R1 | 50 nM | 60 (with hCTLA4-bio) + 30 (with beads) | Standard | | | | |
| R2 | 5 nM | 20 (with hCTLA4-bio) + 30 (with beads) | Standard | | | | 300 nM* |
| R3 | 20 nM mCTLA4 | 60 (with mCTLA4-bio) + 30 (with beads) | Standard | | | | |
| R4 | 5 nM | 10 (with hCTLA4-bio) + 20 (with beads) | Standard + 10 | | 60° C., 3 hours | | 200 nM** |
| R5 | 5 nM | 5 (with hCTLA4-bio) + 10 (non-bio CTLA4) + 20 (with beads) | Standard + 30 | | | | 200 nM** |
| R6 | 2 nM | 5 (with hCTLA4-bio) + 10 (non-bio CTLA4)(*1000) + 15 (with beads) | Standard + 120 | X | | pH 6.3 pH 5.5 | 200 nM** |

*Pre-selection with CD28-Fc
**CD28-Fc added at the same time as bio-CTLA4

The first round of selection (R1) enriched the members of starting libraries AL-1014-01, AL-1014-02, AL-104-03 and AL-1014-04 for binders to biotinylated CTLA4-Fcγ (50 nM). The enrichment for functional binders was confirmed by sequencing.

The output from R1 was a pool of phage clones from each starting library, enriched for functional binders. The output from libraries AL-104-03 and AL-1014-04 was subsequently combined into a new library AL-1014-05. The output from libraries AL-1014-01, AL-1014-02 and AL-1014-04 was combined into a further new library, AL-1014-06. Members of libraries AL-1014-05 and AL-1014-06 were then subjected to 5 additional rounds of screening (R2 to R6), to select for increased binding to CTLA-4 and decreased binding to CD28.

The strategy for the additional 5 rounds of selection was to apply selection pressure specifically aimed at improving the properties of affinity, on-rate, off-rate, selectivity, multimerization and epitope maintenance.

Selection for increased affinity was achieved by lowering the antigen concentration in each round. The selections started at 50 nM CTLA-4 lowering to 5 nM which was maintained in rounds R2, R4 and R5, followed by a final round (R6) in which the CTLA-4 concentration was 2 nM. Selection for increased on-rate was achieved by shortening of incubation time with biotinylated CTLA-4. Selection for decreased off-rate was achieved by increasing the stringency during the wash step. Selection for increased selectivity for CTLA-4 (and reduced binding affinity to CD28) was achieved by incubating in excess of unbiotinylated CD28-Fc (in R2, R4, R5 and R6). Retained binding affinity to mouse CTLA-4 was ensured by including a round (R3) in which biotinylated murine CTLA-4 was used in place of human CTLA-4 as the selection antigen. This step was included to make sure that the affinity to mouse CTLA4 was kept to enable proof-of-concept experiments in mice models. Selecting for avidity effects was avoided by introducing unbiotinylated CTLA-4 five minutes after the start of incubation with biotinylated CTLA-4 (in R5 and R6). Addition of unbiotinylated Fcγ (IgG) to the selection buffer was performed to avoid selecting for binders to the Fc-fusion part of the CTLA-4 antigen.

Decreased temperature sensitivity and potentially increased melting point was obtained by introducing a selection step at increased temperature (60° C.) (R4). Increased affinity at low pH was addressed by introducing a selection round at a lower pH (R6).

After the selection rounds individual phage clones from R5 and R6 were analysed by high throughput screening in a conventional affinity ELISA assay. The assay was a sandwich ELISA which measured binding of phages to either CTLA-4 or CD28. In short, 96-well flat bottom high binding plates (GREINER® #655074) were coated with either CTLA4- Fcγ(Orencia, Apoteket) or CD28- Fcγ (R&D SYSTEMS® 342-CD) by incubating overnight at 4° C. The plates were washed (Wash buffer: PBS+0.05% TWEEN® 20 (PBST) MEDICAGO® #09-9410-100) and then blocked in PBST+3% Milk powder (Semper). The plates were washed again and sample or controls were added to the wells. The samples were incubated for 1 h at room temperature and then washed. Detection antibody, mouse-anti-M13-HRP (GE® Healthcare, #27-9421-01) was added and the plates were subsequently developed using SUPERSIGNAL® Pico Chemiluminescent substrate (Thermo #37069) and detected with an ENVISION™ reader ( PERKINELMER®).

Example 2

Expression and Recloning of Selected Polypeptides

The phage clones selected from Example 1 were re-cloned according to standard protocols into a fusion protein-format, with each clone fused to γ2/γ4 Fc. The fusion proteins were expressed in HEK293 cells. Supernatants culure of the cells were collected and the expressed fusion proteins were assayed using both ELISA and BIACORE™ according to the methods set out below. The results are shown in Table 4, which also shows the mutations present in each clone. The best performing clone in the ELISA assay (907) had an EC50 binding ratio almost 10 times higher than wild-type protein CD86. The best performing clone in the BIACORE™ assay (904) had a Kd binding ratio more than 4 times higher than wild type protein CD86.

Binding ELISA 96-well flat bottom high binding plates (GREINER® #655074) were coated with either CTLA4-Fc (Fitzgerald #30R-CD152) or CD28-Fc (R&D SYSTEMS® 342-CD) by incubating overnight at 4° C. The plates were washed (Wash buffer: PBS+0.05% TWEEN® 20 (PBST) MEDICAGO® #09-9410-100) and then blocked in PBST+3% BSA (MERCK®, #1.12018.0100). The plates were washed again and sample or controls (serially diluted ⅕ from 200-0.001 μg/ml) were added to the wells. The samples were incubated for 1h at room temperature and then washed. Detection antibody, goat-anti-human IgG Fcγ-HRP (Jackson, #109-035-098) was added and the plates were subsequently developed using SUPERSIGNAL® Pico Chemiluminescent substrate (Thermo #37069) and detected with an ENVISION™ reader ( PERKINELMER®). EC50 values were calculated for both CTLA4 and CD28. The binding ratio (EC50 binding ratio =[EC50 for CD28]÷[EC50 for CTLA-4]) was calculated for each polypeptide and is shown in Table 4.

BIACORE™

Either CTLA4-Fc (Fitzgerald #30R-CD152) or CD28-Fc (R&D systems 342-CD) was immobilized to the BIACORE™ senshorship, CM5, using conventional amine coupling. The CD86 mutant molecules and controls (serially diluted ½ 100-1.5 nM) were analyzed for binding in HBs-P (GE, BR-1003-69) at a flow rate 30 µl/ml. The association was followed for 3 minutes and the dissociation for 10 minutes. Regeneration was performed twice using 5 mM NaOH for 30 seconds. The kinetic parameters and the affinity constants were calculated using BIAevaluation 4.1 software. The binding ratio (Kd binding ratio =[Kd for CD28]÷[Kd for CTLA-4]) was calculated for each polypeptide and is shown in Table 4.

Example 3

Expanded Library Diversity and Repeated Selection and Screening

Library Production

The starting material for two further libraries, AL-1014-11 and AL-1014-12, were six clones identified in Examples 1 and 2, namely 901, 904, 906, 907, 908, 915. Additional diversity was generated by error-prone PCR with mutated oligos included in the reassembly PCR step, in accordance with protocols described in WO2002048351, WO200309734, and WO2007057682. The applied oligos comprised mutations in hotspot regions of the CD86 molecules. Approximately 20 clones from each library were sequenced. The two libraries contained recombined clones, error prone PCR generated clones, and clones produced by the introduction of mutated oligos. Each clone contained on average 3-11 mutations compared to the wild-type sequence of CD86.

TABLE 4

| Clone | Mutated positions and amino acid change (positions numbered as in FIG. 4) | EC50 binding ratio | Kd binding ratio |
|---|---|---|---|
| 900 | H79D, L107I, I111V, T118S, M120L, I121V, R122K, Q125E | 3.5 | ND* |
| 901 | Q48L, S49T, L107I, I111V, R122K, Q125E, A134T | 17.2 | 2.7 |
| 904 | V54I, K74R, S77A, H79D, L107I, T118S, I121V, R122K, N127D | 12.2 | 6.8 |
| 906 | F32I, Q48L, K74R, H79D, L107F, M120L, I121V, R122K, Q125E | 16.2 | 0.8 |
| 907 | R122K, Q125E | 30.5 | 5.6 |
| 908 | L107I, I121V, R122K, Q125E | 6.2 | 4.7 |
| 910 | H79D, L107I, I121V, R122K, Q125E | 7.7 | 5.1 |
| 915 | V64I, H79D, L107F, T118S, M120L, R122K, N127D | 9.9 | 1.9 |
| 938 | V64I, L107I, I121V, R122K | 2.0 | 5.5 |
| | Wild type | 3.4 | 1.6 |

*No detectable binding was seen in the BIAcore ™ analysis

Table 5 summarises the mutations and positions in each of the selected clones. The full amino acid sequences for clones 900, 901, 904, 906, 907, 908, 910, 915 and 938 are provided as SEQ ID NOs: 6 to 14, respectively.

TABLE 5

| | F32I | Q48L | S49T | V54I | V64I | K74R | S77A | H79D | L107I/F |
|---|---|---|---|---|---|---|---|---|---|
| 900 | | | | | | | | D | I |
| 901 | | L | T | | | | | | I |
| 904 | | | | I | | R | A | D | I |
| 906 | I | L | | | | R | | D | F |
| 907 | | | | | | | | | |
| 908 | | | | | | | | | I |
| 910 | | | | | | | | D | I |
| 915 | | | | | I | | | D | F |
| 938 | | | | | I | | | | I |

| | I111V | T118S | M120L | I121V | R122K | Q125E | N127D | A134T |
|---|---|---|---|---|---|---|---|---|
| 900 | V | x | L | v | K | E | | |
| 901 | V | | | | K | E | | T |
| 904 | | S | | v | K | | D | |
| 906 | | | L | v | K | E | | |
| 907 | | | | | K | E | | |
| 908 | | | | v | K | E | | |
| 910 | | | | v | K | E | | |
| 915 | | S | L | | K | | D | |
| 938 | | | | v | K | | | |

Selection Strategy

Selection rounds R2 to R6 as described in Example 1 were applied to both libraries AL-1014-11 and AL-1014-12. Clones selected in the last two rounds were sequenced to confirm that recombination and novel mutations were achieved.

Assesment of Selected Clones

Approximately 1250 clones from the last two selection rounds were expressed as phage stocks and analyzed for binding to CTLA-4 and CD28 by the same high throughput screening ELISA as described in Example 1 (data not shown). Clones were ranked based on their binding to CTLA-4 and CD28. The top ten clones were selected based on the criteria of high binding to CTLA-4 and low binding to CD28. The sequence of these clones was determined and each was expressed from HEK293 cells as a gamma2/gamma4 fusion, as described in Example 2.

Table 6 summarises the mutations and positions in each of the top ten clones. The full amino acid sequences for clones 1038, 1039, 1040, 1041, 1042, 1043, 1044, 1045, 1046 and 1047 are provided as SEQ ID NOs: 15 to 24, respectively.

TABLE 6

| | F32L | Q48L | S49T | K74I/R | H79D/S/A | K103E | L107I/R |
|---|---|---|---|---|---|---|---|
| 1038 | | L | | | D | | I |
| 1039 | | L | | | S | | I |
| 1040 | | L | | R | D | | R |
| 1041 | L | L | | | D | | I |
| 1042 | | L | | I | S | | I |
| 1043 | | L | | | D | | I |
| 1044 | | L | T | | S | | I |
| 1045 | | L | T | | D | | |
| 1046 | | | | | D | E | I |
| 1047 | | L | | | D | | I |

| | T118S | M120L | I121V | R122K/N | Q125E | N127S/D |
|---|---|---|---|---|---|---|
| 1038 | | | V | K | E | |
| 1039 | S | | V | K | | D |
| 1040 | | | | N | | |
| 1041 | | L | V | K | E | |
| 1042 | S | | V | K | | D |
| 1043 | | | | K | E | |
| 1044 | | | | K | E | S |
| 1045 | | L | V | K | E | |
| 1046 | S | | V | K | | D |
| 1047 | | L | V | K | E | |

Example 4

Further Assessment of Top Ten Polypeptides

The polypeptides from each of the ten clones selected in Example 3 were further characterised as follows.

Expression and purification

Plasmids encoding each clone were transfected into FREESTYLE™ 293-T cells (Invitrogen) according to standard protocols and supernatants were harvested on day 6. Polypeptides and controls were affinity purified using protein A columns (GE® Healthcare #17-0402-01).

Binding ELISA

Similar to the protocol described in Example 2, 96-well flat bottom high binding plates (GREINER® #655074) were coated with either CTLA4-Fc (Fitzgerald #30R-CD152) or CD28-Fc (kindly provided by Simon Davis, Oxford University) by incubating overnight at 4° C. The plates were washed (Wash buffer: PBS+0.05% TWEEN® 20 (PBST) MEDICAGO® #09-9410-100) and then blocked in PBST+3% BSA (MERCK®, #1.12018.0100). The plates were washed again and sample or controls (serially diluted ⅓ from 50 000-0001 nM) were added to the wells. The samples were incubated for 1h at room temperature and then washed. Detection antibody, goat-anti-human IgG Fcγ-HRP (Jackson, #109-035-098) was added and the plates were subsequently developed using SUPERSIGNAL® Pico Chemiluminescent substrate (Thermo #37069) and detected with an ENVISION™ reader (PERKINELMER®).

The results of the CTLA-4 binding ELISA are shown in FIG. 1. EC50 values were calculated and are shown in Table 7. All molecules showed better EC50 values than both wild type and H79A, with an improvement of between 2 and 67-fold. Binding to CD28 was too low for detection by this assay (data not shown).

TABLE 7

| Sample | EC50 |
|---|---|
| 1038 | 0.14 |
| 1039 | 0.039 |
| 1040 | 0.0076 |
| 1041 | 0.087 |
| 1042 | 0.29 |
| 1043 | 0.035 |
| 1044 | 0.029 |
| 1045 | 0.047 |
| 1046 | 0.019 |
| 1047 | 0.037 |
| Wild type | 0.51 |
| Prior Art | 0.81 |
| Negative control | No activity |

Figure 2:
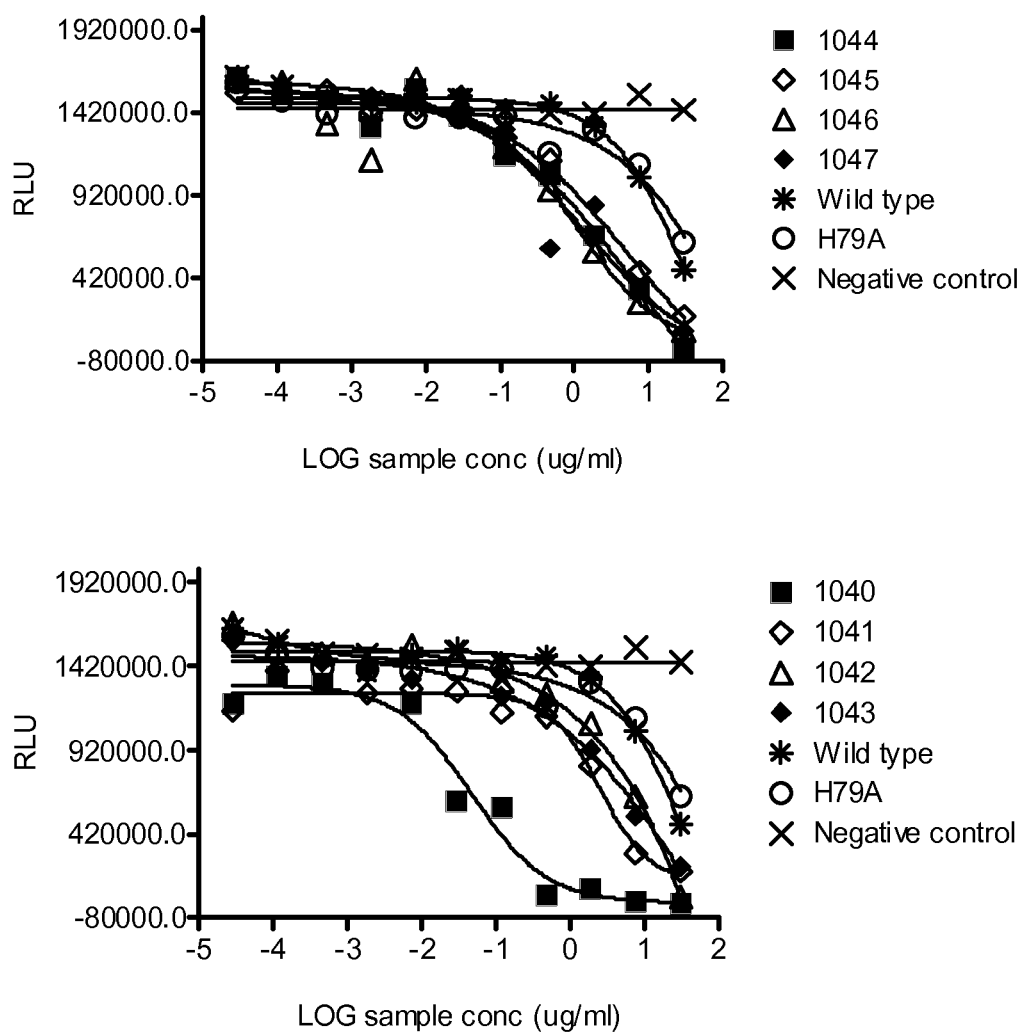
FIG. 2 shows the CTLA-4 binding properties of polypeptides of the invention as determined by an ELISA inhibition assay.

Inhibition ELISA 96-well flat bottom high binding plates (GREINER® #655074) were coated with wildtype CD86-Fc (R&D SYSTEMS® #7625-B2) by incubating overnight at 4° C. The plates were washed (Wash buffer: PBS+0.05% TWEEN® 20 (PBST) MEDICAGO® #09-9410-100) and then blocked in PBST+3% BSA (MERCK®, #1.12018.0100). The sample (CD86 mutant or wild type protein; serially diluted ¼ from 30000 to 0.3 ng/ml) was incubated with biotinylated-CTLA4 (Fitzgerald #30R-CD 152) in room temperature 1 h, the mixture was then added to the blocked wells in the blocked wells in the ELISA plate. Detection was performed with Streptavidin-HRP (PIERCE® #21126) and the plates were subsequently developed using SUPERSIGNAL® Pico Chemiluminescent substrate (Thermo #37069) and detected with ENVISION™ reader ( PERKINELMER®). The results are shown in FIG. 2. IC50 values were calculated and are shown in Table 8. All molecules showed better IC50 value than both wild type and H79A, the IC of the best mutant CD86 molecule was improved over 100 fold compared to wild type.

TABLE 8

| Sample | IC50 |
|---|---|
| 1040 | 0.049 |
| 1041 | 3.1 |
| 1042 | 4.3 |
| 1043 | 4.0 |
| 1044 | 1.4 |
| 1045 | 2.6 |
| 1046 | 1.1 |
| 1047 | 0.98 |
| Wild type | 15 |
| H79A | 25 |
| Negative control | No activity |

BIACORE™

As in Example 2, either CTLA4-Fc (Fitzgerald #30R-CD152) or CD28-Fc (kindly provided by Simon Davis, Oxford University) was immobilized to the BIACORE-™senshorship, CM5, using conventional amine coupling. The CD86 mutant molecules and controls (serially diluted ⅓ 1000-4 nM) were analyzed for binding in HBs-P (GE®, BR-1003-69) at a flow rate 30 µl/ml. The association was followed for 3 minutes and the dissociation for 10 minutes. Regeneration was performed twice using 5 mM NaOH for 30 seconds. The kinetic parameters and the affinity constants were calculated using BIAevaluation 4.1 software.

The CTLA-4 results for each selected clone and wild type CD86 to CTLA-4 are summarised in Table 9. The mutations present in each clone are also shown. A clone including only the H79A mutation from Peach et at (Journal of Biological Chemistry 1995, vol 270(36), 21181-21187) was also included for comparison. The CD28 results are not shown, since in most cases affinity to CD28 was too weak to be determined by this protocol. However, where it was determined, the affinity of the selected CD86 clones for CD28 was at least 100 times lower than that for CTLA-4.

It was also determined that the selected clones also bind to murine CTLA-4 (data not shown).

TABLE 9

| Clone | Mutated positions and amino acid change (positions numbered as in FIG. 4) | ka (1/Ms) | kd (1/s) | Kd (nM) |
|---|---|---|---|---|
| 1038 | Q48L, H79D, L107I, I121V, R122K, Q125E | 1.0e6 | 0.012 | 12 |
| 1039 | Q48L, H79S, L107I, T118S, I121V, R122K, N127D | 1.0e6 | 8.5e-3 | 8 |
| 1040 | Q48L, K74R, H79D, L107R, R122N | 1.0e6 | 3.2e-3 | 3 |
| 1041 | F32L, Q48L, H79D, L107I, M120L, I121V, R122K, 125E | 7.0e5 | 8.4e-3 | 12 |
| 1042 | Q48L, K74I, H79S, L107I, T118S, I121V, R122K, N127D | 4.4e5 | 0.011 | 25 |
| 1043 | Q48L, H79D, L107I, R122K, Q125E | 1.1e6 | 0.011 | 10 |
| 1044 | Q48L, S49T, H79S, L107I, R122K, Q125E, N127S | 1.1e6 | 9.4e-3 | 8 |
| 1045 | Q48L, S49T, H79D, M120L, I121V, R122K, Q125E | 9.4e5 | 8.3e-3 | 9 |
| 1046 | H79D, K103E, L107I, T118S, I121V, R122K, N127D | 1.4e6 | 8.0e-3 | 6 |
| 1047 | Q48L, H79D, L107I, M120L, I121V, R122K, Q125E | 8.5e5 | 8.4e-3 | 10 |
| Wild type | | 4.6e5 | 0.023 | 50 |
| H79A | | 3.4e5 | 0.022 | 63 |

Example 5

Anti-Tumor Activity of Exemplary Polypeptide from Clone 904

Figure 3:
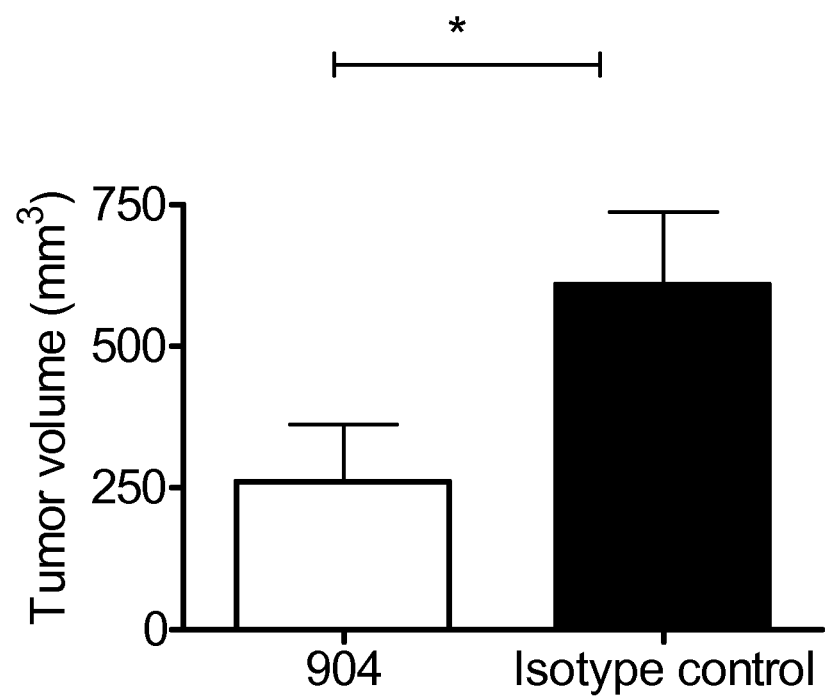
FIG. 3 shows the anti-tumour activity of an exemplary polypeptide of the invention. The polypeptide showed a significant anti-tumor effect as compared to the control ($*p<0.05$).

The anti-tumour activity of an exemplary mutant CD86 molecule of the invention, 904, was studied in a C57BL/6 mouse model inoculated with murine bladder cancer cells. In brief, $2.5 \times 10^5$ murine bladder cancer cells, MB49, were subcutaneously injected into the right flank of C57BL/6 mice (n=8 per group). On day 7, 10 and 13 the mutant CD86 molecule of the invention (904), or an isotype control, was administered to the animals by peritumoral (p.t.) injection to the primary tumor in 100 µl doses. Tumor growth and survival was monitored throughout the experiment using a caliper and tumor size was calculated by the ellipsoid volume formula: $=4/3*\pi*a$(radius of length)*b(radius of width)*c(radius of depth). Mice were sacrificed if the tumor exceeded 1 cm$^3$ or if ulcers developed. The results are shown in FIG. 3. Tumor volume data is presented at day 23 when the first mice was sacrificed due to ethical considerations. The mutant CD86 molecule showed a significant tumor effect as compared to the control (*p<0.05).

Example 6

Cross Reactivity to Murine CTLA-4 of Exemplary Polypeptide from Clone 1040

The relative affinity for murine and human CTLA-4 of an exemplary mutant CD86 molecule of the invention, 1040, was investigated using an inhibition ELISA binding assay. The 1040 molecule used in these experiments was conjugated to an anti-CD40 antibody as part of a bispecific molecule. The CTLA-4 binding properties of the CD86 molecule are not affected by this conjugation (data not shown).

In brief, 96-well flat bottom plate high binding plates (GREINER® #655074) were coated with human CTLA-4 (Fitzgerald) incubating overnight at 4° C. The plates were washed (Wash buffer: PBS+0.05% TWEEN® 20 (PBST) MEDICAGO® #09-9410-100) and then blocked in PBST+ 3% BSA (MERCK®, #1.12018.0100).

The sample (exemplary CD86 mutant) was pre-incubated at room temperature for 1 hour with soluble biotinylated human CTLA4 (Fitzgerald #30R-CD152) or soluble murine CTLA-4 (R&D systems) at different concentrations (serial dilutions ¼ from 30000 to 0.3 ng/ml).

Figure 5:
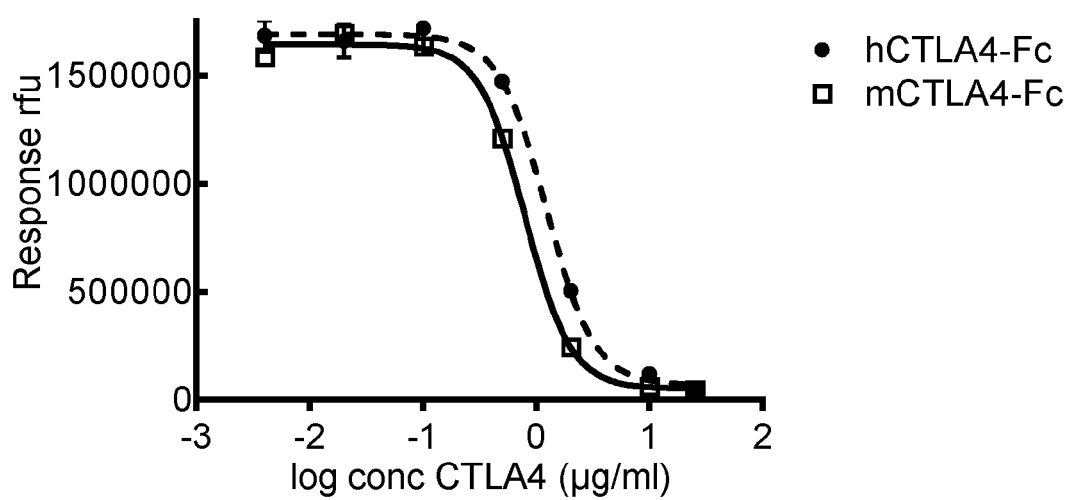
FIG. 5 shows the results of an inhibition ELISA demonstrating that a polypeptide of the invention has binding affinity of a similar magnitude for both human and murine CTLA-4.

The mixture was then added to the blocked wells in the ELISA plate. Detection was performed with Streptavidin-HRP (PIERCE® #21126) and the plates were subsequently developed using SUPERSIGNAL® Pico Chemiluminescent substrate (Thermo #37069) and detected with ENVISION™ reader (PERKINELMER®). The results are shown in FIG. 5. The observed inhibition curves with murine and human CTLA-4 demonstrate that the binding affinity of the exemplary CD86 mutant (1040) to the two forms of CTLA-4 is of a similar magnitude.

The invention claimed is:

1. A polypeptide comprising an amino acid sequence selected from the group consisting of SEQ ID Nos: 6 to 24, wherein said polypeptide binds to cytotoxic T-lymphocyte-associated protein 4 (CTLA-4) with higher affinity than wild-type human cluster of differentiation 86 (CD86).

2. The polypeptide according to claim 1, wherein the ratio of either (a) [$K_d$ for cluster of differentiation 28 (CD28)]÷[$K_d$ for CTLA-4]; or (b) [$EC_{50}$ for CD28]÷[$EC_{50}$ for CTLA-4] is higher than the corresponding ratio of wild-type human CD86.

3. The polypeptide according to claim 1, wherein said polypeptide inhibits signalling from CTLA-4 or increases the activity of a cell expressing CTL-4, and optionally wherein said CTLA-4 is human or murine CTLA-4.

4. The polypeptide according to claim 1, wherein said polypeptide is attached to a molecule selected from the group consisting of an immunoglobulin fragment crystallisable (Fc) region, an immunoglobulin (Ig) domain, polyethylene glycol (PEG), a therapeutic agent and a detectable label.

5. A composition comprising a polypeptide according to claim 1 and at least one pharmaceutically acceptable diluent or carrier.

6. A method of increasing the activation of a cell expressing CTLA-4, the method comprising administering to said cell a polypeptide according to claim 1.

* * * * *